(12) United States Patent
Nicolaou et al.

(10) Patent No.: US 7,358,266 B2
(45) Date of Patent: Apr. 15, 2008

(54) CYCLOPROPYL AND CYCLOBUTYL EPOTHILONE ANALOGS

(75) Inventors: Kyriacos C. Nicolaou, La Jolla, CA (US); Kenji Namoto, Solana Beach, CA (US); Andreas Ritzen, Vanlose (DK); Mitsuru Shoji, Tokyo (JP); Trond Ulven, Copenhagen (DK); Karl-Heinz Altmann, Reinach (CH)

(73) Assignee: The Scripps Research Institute, La Jolla, CA (US)

(*) Notice: Subject to any disclaimer, the term of this patent is extended or adjusted under 35 U.S.C. 154(b) by 827 days.

(21) Appl. No.: 10/227,073

(22) Filed: Aug. 23, 2002

(65) Prior Publication Data

US 2004/0039026 A1    Feb. 26, 2004

Related U.S. Application Data

(60) Provisional application No. 60/314,698, filed on Aug. 23, 2001.

(51) Int. Cl.
*A61K 31/425* (2006.01)
*C07D 277/30* (2006.01)
*X07D 277/04* (2006.01)

(52) U.S. Cl. .............. 514/370; 514/390; 548/204; 548/110; 548/182; 548/186

(58) Field of Classification Search .......... 548/204, 548/110, 182, 186; 514/370, 390
See application file for complete search history.

(56) References Cited

U.S. PATENT DOCUMENTS 5,969,145 A * 10/1999 Schinzer et al. .......... 548/110

(Continued)

FOREIGN PATENT DOCUMENTS

WO        WO 98/25929        6/1998

(Continued)

OTHER PUBLICATIONS

Iee, J Org Chem, vol. 65, pp. 6525-6533, 2000.*

(Continued)

*Primary Examiner*—D. Margaret Seaman
(74) *Attorney, Agent, or Firm*—Donald G. Lewis; Thomas Fitting

(57) ABSTRACT

The invention relates to cis- and trans-12, 13-cyclopropyl and 12,13-cyclobutyl epothilones of formula I to IV

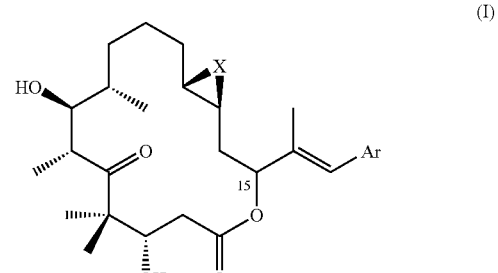

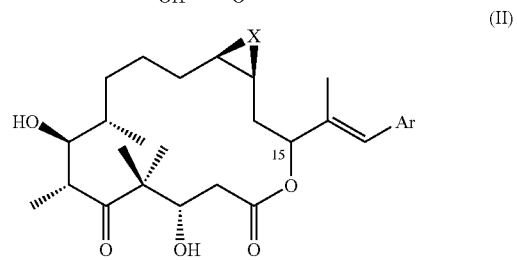

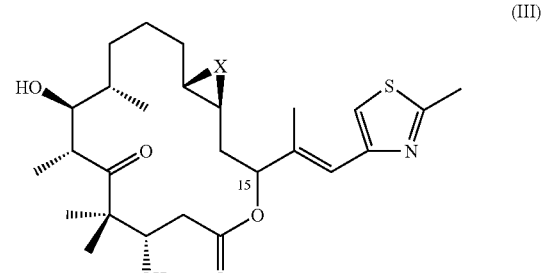

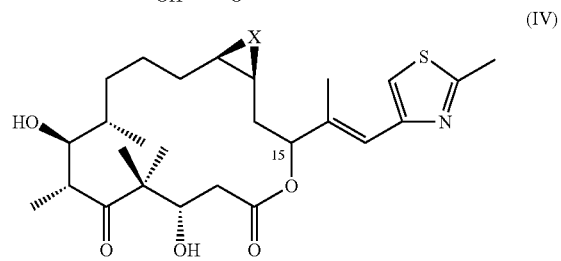

wherein Ar is a radical represented by the following structure:

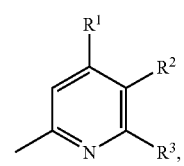

and the other radicals and symbols have the meanings as defined herein; to their chemical synthesis and biological evaluation; their use in the treatment of neoplastic diseases and to pharmaceutical preparations containing such compounds. The compounds described herein are potent tubulin polymerization promoters and cytotoxic agents.

23 Claims, 16 Drawing Sheets

U.S. PATENT DOCUMENTS

| | | | | |
|---|---|---|---|---|
| 6,043,372 | A | * | 3/2000 | Schinzer et al. ............ 548/110 |
| 6,156,905 | A | * | 12/2000 | Schinzer et al. ............ 548/204 |
| 6,380,394 | B1 | * | 4/2002 | Nicolaou et al. ........... 548/125 |
| 6,531,497 | B1 | * | 3/2003 | Nicolaou et al. ........... 514/370 |

FOREIGN PATENT DOCUMENTS

| | | |
|---|---|---|
| WO | WO 99/54318 | 4/1999 |
| WO | WO 00/47584 | 8/2000 |

OTHER PUBLICATIONS

Dale, et al., "α-Methoxy-α-trifluoromethylphenylacetic Acid, a Versatile Reagent for the Determination of Enantiomeric Composition of Alcohols and Amines", *J. Org. Chem. 34*: 2543-2549 (1969).

Dale, et al., "Nuclear Magnetic Resonance Enantiomer Reagents. Configurational Correlations via Nuclear Magnetic Resonance Chemical Shifts of Diastereomeric Mandelate. O-Methylmandelate, and α-Methoxy-α-trifluoromethylphenylacetate (MTPA) Esters", *J. Am. Chem. Soc. 95*: 512-519 (1973).

Inanaga, et al., "A Rapid Esterification by Means of Mixed Anhydride and Its Application to Large-ring Lactonization", *Bull. Chem. Soc. Jpn. 52*: 1989-1993 (1979).

Trost, et al. "Cyclization Catalyzed by Palladium(0). Initial Studies and Macrolide Formation", *J. Am. Chem. Soc. 102*: 4743-4763 (1980).

Takai, et al., "Selective Grignard-Type Carbonyl Addition of Alkenyl Halides Mediated by Chromium(II) Chloride", *Tetrahedron Lett. 24*: 5281-5284 (1983).

Kasel, et al., "Preparations of Chiral Hydroxyester Synthons via Stereoselective Porcine Pancreatic Lipase-catalyzed Hydrolyses of *meso*- Diesters", *J. Chem. Soc., Chem. Commun.*: 1563-1564 (1985).

Laumen, et al., "Enantioselective Hydrolysis of *cis*-1,2-Diacetoxycycloalkanedimethanols: Enzymatic Preparation of Chiral Building Blocks from Prochiral *Meso*-Substrates", *Tetrahedron Lett. 26*: 2073-2076 (1985).

Jin, et al., "Catalytic Effect of Nickel(II) Chloride and Palladium(II) Acetate on Chromium(II)-Mediated Coupling Reaction of Iodo Olefins with Aldehydes", *J. Am. Chem. Soc. 108*: 5644-5646 (1986).

Brown, et al., "Selective Reductions. 40. A Critical Examination of the Relative Effectiveness of Various Reducing Agents for the Asymmetric Reduction of Different Classes of Ketones", *J. Org. Chem. 52*: 5406-5412 (1987).

Skehan, et al., "New Colorimetric Cytotoxicity Assay for Anticancer-Drug Screening", *J. Natl. Cancer Inst. 82*: 1107-1112 (1990).

Brown, et al., "Asymmetric Reduction with Chiral Organoboranes Based on α-Pinene", *Acc. Chem. Res. 25*: 16-24 (1992).

Mulzer, et al., "Total Synthesis of 6-Epi-Erythronolide Derivatives", *Synthesis*: 215-228 (1992).

Arcadi, et al., "2-Substituted-3-acylindoles through the Palladium-Catalysed Carbonylative Cyclization of 2-Alkynyltrifluoroacetanilides with Aryl Halides and Vinyl Triflates", *Tetrahedron 50*: 437-452 (1994).

Grandjean, et al., "An Improved Procedure for Aldehyde-to-Alkyne Homologation via 1,1-Dibromoalkenes; Synthesis of 1-Bromoalkynes", *Tetrahedron Lett. 35*: 3529-3530 (1994).

Azzena, et al., "Regiochemical Control of the Ring Opening of 1,2-Epoxides by Means of Chelating Processes. 10. Synthesis and Ring Opening Reactions of Mono- and Difunctionalized cis and trans Aliphatic Oxirane Systems", *Tetrahedron 51*: 10601-10626 (1995).

Taber, et al., "Diastereoselective Synthesis of an Isoprostane: (±)-8-epi-PGF$_{2\alpha}$Ethyl Ester", *J. Org. Chem. 62*: 194-198 (1997).

Betzer, et al., "An Efficient Method in Stannylcupration of a Methyl Substituted Enyne of Alkyne by Kinetic Control Using Methanol", *Tetrahedron Lett. 38*: 2279-2282 (1997).

Nicolaou. et al., "Total Syntheses of Epothilones A and B via a Macrolactonization-Based Strategy", *J. Am. Chem. Soc. 119*: 7974-7991 (1997).

Giannakakou, et al., "Paclitaxel-resistant Human Ovarian Cancer Cells Have Mutant β-Tubulins That Exhibit Impaired Paclitaxel-driven Polymerization", *J. Biol. Chem. 272*: 17118-17125 (1997).

Nicolaou, et al., "Designed Epothilones: Combinatorial Synthesis, Tubulin Assembly Properties, and Cytotoxic Action against Taxol-Resistant Tumor Cells", *Angew. Chem. Int. Ed. Engl. 36*: 2097-2103 (1997).

Nicolaou, et al., "Synthesis and biological properties of C12.13-cyclopropylepothilone A and related epothilones", *Chem. Biol. 5*: 365-372 (1998).

Nicolaou, et al., "Chemical Biology of Epothilones", *Angew. Chem. Int. Ed. Engl. 37*: 2015-2045 (1998).

Charette, et al., "Enantioselective Cyclopropanation of Allylic Alcohols with Dioxaborolane Ligands: Scope and Synthetic Applications", *J. Am. Chem. Soc. 120*: 11943-11952 (1998).

Nicolaou, et al., "Total Synthesis of 16-Desmethylepothilone B. Epothilone B$_{10}$- Epothilone F. and Related Side Chain Modified Epothilone B Analogues", *Chem. Eur. J. 6*: 2783-2800 (2000).

Nicolaou, et al., "Chemical Synthesis and Biological Properties of Pyridine Epothilones", *Chem. Biol. 7*: 593-599 (2000).

Giannakakou, et al., "A common pharmacophore for epothilone and taxanes: Molecular basis for drug resistance conferred by tubulin mutations in human cancer cells", *Proc. Natl. Acad. Sci. USA 97*: 2904-2909 (2000).

Johnson et al., "Synthesis Structure Proof, and Biological Activity of Epothilone Cyclopropanes", *Org. Lett. 2*: 1537-1540 (2000).

Altmann, et al., "Synthesis and Biological Evaluation of Highly Potent Analogues of Epothilones B and D", *Bioorg. Med. Chem. Lett. 10*: 2765-2768 (2000).

Nicolaou, et al., "Synthesis and Biological Evaluation of 12, 13-Cyclopropyl and 12. 13-Cyclobutyl Epothilones", *CHEMBIOCHEM*: 69-75 (2001).

Nicolaou, et al., "Chemical Synthesis and Biological Evaluation of *cis*- and *trans*-12. 13-Cyclopropyl and 12. 13-Cyclobutyl Epothilones and Related Pyridine Side Chain Analogues", *J. Am. Chem. Soc. 123*: 9313-9323 (2001).

* cited by examiner

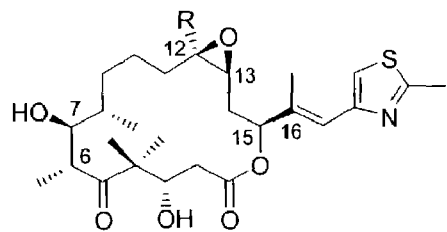

1: R = H : epothilone A (Epo A)
2: R = Me : epothilone B (Epo B)

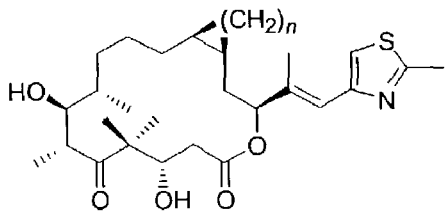

3: n = 1: (12S,13S,15S)-cyclopropyl epothilone A [cis-(15S)-CP-epo]
4: n = 2: (12S,13S,15S)-cyclobutyl epothilone A [cis-(15S)-CB-epo]

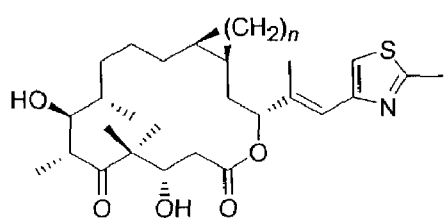

5: n = 1: (12S,13S,15R)-cyclopropyl epothilone A [cis-(15R)-CP-epo]
6: n = 2: (12S,13S,15R)-cyclobutyl epothilone A [cis-(15R)-CB-epo]

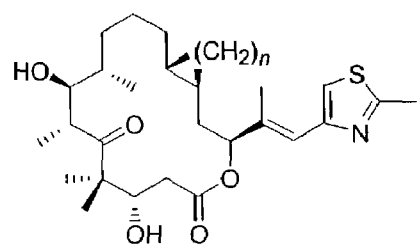

7: n = 1: (12R,13S,15S)-cyclopropyl epothilone A [trans-(15S)-CP-epo]
8: n = 2: (12R,13S,15S)-cyclobutyl epothilone A [trans-(15S)-CB-epo]

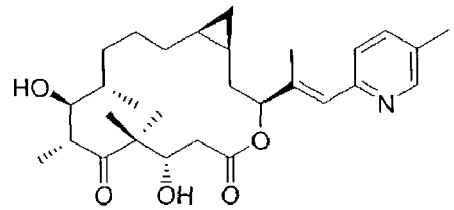

9: (12S,13S,15S)-cyclopropyl 5-methylpyridine epothilone A [cis-(15S)-CP-py-epo]

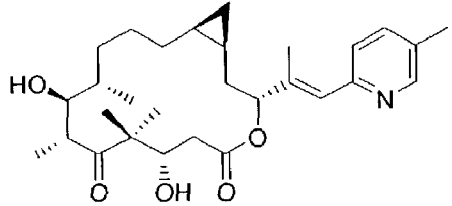

10: (12S,13S,15R)-cyclopropyl 5-methylpyridine epothilone A [cis-(15R)-CP-py-epo]

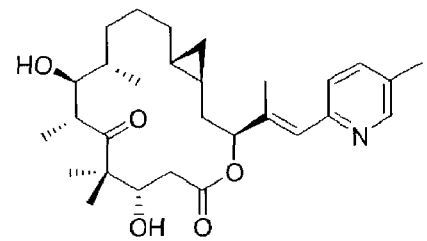

11: (12R,13S,15S)-cyclopropyl 5-methylpyridine epothilone A [trans-(15S)-CP-py-epo]

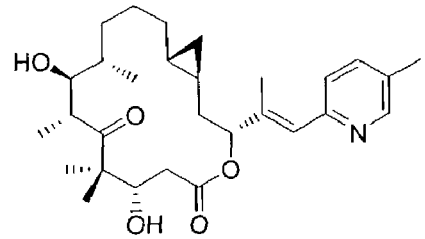

12: (12R,13S,15R)-cyclopropyl 5-methylpyridine epothilone A [trans-(15R)-CP-py-epo]

Figure 1

Cytotoxicity of epothilones 1 through 12 and paclitaxel against 1A9 human ovarian carcinoma cells and β-tubulin mutant cell lines selected with paclitaxel or epothilone A.[a]

| | Cell line | | | | | | |
|---|---|---|---|---|---|---|---|
| | 1A9 | A8 (β274) | | PTX10 (β270) | | PTX22 (β364) | |
| Compound | $IC_{50}$ | $IC_{50}$ | RR | $IC_{50}$ | RR | $IC_{50}$ | RR |
| epothilone A (Epo A) 1 | 2.37 ± 0.433 | 117 ± 27.01 | 49.3 | 23.35 ± 1.85 | 9.9 | 5.21 ± 0.344 | 2.2 |
| epothilone B (Epo B) 2 | 0.095 ± 0.007 | 2.14 ± 0.072 | 22.5 | 0.548 ± 0.156 | 5.8 | 0.163 ± 0.02 | 1.7 |
| paclitaxel (Taxol®) | 1.77 ± 0.227 | 17.95 ± 3.08 | 10.14 | 52.75 ± 9.4 | 29.9 | 28.5 ± 2.75 | 16.1 |
| cis-(15S)-CP-epo 3 | 1.60 ± 0.124 | 23.43 ± 4.29 | 14.6 | 10.9 ± 1.4 | 6.8 | 2.6 ± 0.2 | 1.6 |
| cis-(15S)-CB-epo 4 | 8.8 ± 0.00 | 196 ± 0.00 | 22.2 | 62 ± 0.00 | 7.1 | 20 ± 0.00 | 2.3 |
| cis-(15R)-CP-epo 5[b] | 225 | >300 (inactive) | na | >300 (inactive) | na | >300 (inactive) | na |
| cis-(15R)-CB-epo 6[b] | 180 | >300 (inactive) | na | >300 (inactive) | na | >300 (inactive) | na |
| trans-(15S)-CP-epo 7 | 2.7 ± 0.100 | 48 ± 0.00 | 17.8 | 14.4 ± 0.00 | 5.3 | 3.7 ± 0.00 | 1.4 |
| trans-(15S)-CB-epo 8 | 25.5 ± 1.50 | >300 (inactive) | >11.7 | 146 ± 0.00 | 5.7 | 63 ± 0.00 | 2.5 |
| cis-(15S)-CP-py-epo 9 | 1.40 ± 0.453 | 53.5 ± 14.57 | 38.2 | 8.15 ± 0.565 | 5.8 | 1.17 ± 0.94 | 0.84 |
| cis-(15R)-CP-py-epo 10 | >300 (inactive) | >300 (inactive) | na | >300 (inactive) | na | >300 (inactive) | na |
| trans-(15S)-CP-py-epo 11 | 0.625 ± 0.175 | 9.5 | 15.2 | 3.49 ± 0.00 | 5.6 | 0.39 ± 0.00 | 0.63 |
| trans-(15R)-CP-py-epo 12 | >300 (inactive) | >300 (inactive) | na | >300 (inactive) | na | nd | na |

[a] The antiproliferative effects of the tested compounds against the parental 1A9 and the paclitaxel- and epothilone-selected drug resistant clones (PTX10, PTX22 and A8, respectively) were assessed in a 72 h growth inhibition assay using the SRB (sulforhodamine-B) assay (Skehan, P.; et al. *J. Natl. Cancer Inst.* 1990, 82, 1107–1112). $IC_{50}$ values for each compound are given in nM and represent the mean of 3-5 independent experiments ± standard error of the mean. Relative resistance (RR) is calculated as an $IC_{50}$ value for each resistant subline divided by that for the parental cell line (1A9). [b] Data from Nicolaou, K. C.; et al. *ChemBioChem* 2001, 1, 69–75. CP = cyclopropyl, CB = cyclobutyl, na = not applicable, nd = not determined, py = 5-methylpyridine side chain.

Figure 15

Tubulin polymerization potency[a] and cytotoxicity[b] of epothilones 1 through 12 and paclitaxel against human epidermoid cancer cell lines.

| Compound | %TP[a] | KB-31[b] | KB-8511[b] |
|---|---|---|---|
| epothilone A (Epo A) 1 | 69 | 2.15 | 1.91 |
| epothilone B (Epo B) 2 | 90 | 0.19 | 0.18 |
| paclitaxel (Taxol®) | 49 | 2.92 | 626 |
| cis-(15S)-CP-epo 3 | 83 | 0.838 | 0.408 |
| cis-(15S)-CB-epo 4 | 79 | 60.7 | 29.7 |
| cis-(15R)-CP-epo 5[b] | 26 | 159.5 | 66.7 |
| cis-(15R)-CB-epo 6[b] | 29 | 378 | 156 |
| trans-(15S)-CP-epo 7 | 100 | 0.971 | 0.641 |
| trans-(15S)-CB-epo 8 | 82 | 23.1 | 11.5 |
| cis-(15S)-CP-py-epo 9 | 100 | 0.618 | 0.446 |
| cis-(15R)-CP-py-epo 10 | 6 | >1000 | >1000 |
| trans-(15S)-CP-py-epo 11 | 94 | 0.835 | 0.676 |
| trans-(15R)-CP-py-epo 12 | <10 | 930 | >1000 |

[a] %TP = percent tubulin polymerized after incubation of tubulin with a known concentration of compound (typically 3 µM). [b] Cytotoxicity towards human cancer cell lines as $IC_{50}$ values given in nM. KB-31: epidermoid Taxol®-sensitive, KB-8511: epidermoid Taxol®-resistant (due to P-gp overexpression).

Figure 16

CYCLOPROPYL AND CYCLOBUTYL EPOTHILONE ANALOGS

CROSS REFERENCE TO RELATED APPLICATIONS

This is a non-provisional application claiming priority under 35 U.S.C. 119(e) from copending U.S. provisional application Ser. No. 60/314,698, filed Aug. 23, 2001.

STATEMENT OF GOVERNMENT SUPPORT

This invention was made with government support under Contract No. CA78045 by the National Institutes of Health. The Government has certain rights in the invention.

FIELD OF INVENTION

The invention is related to analogs of epothilone. More particularly, the invention is directed to analogs of cis- and trans-12,13-cyclopropyl and 12,13-cyclobutyl epothilones.

SUMMARY

One aspect of the invention is directed to compounds represented by any of the following structures:

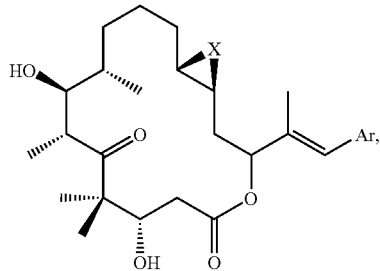
(I)

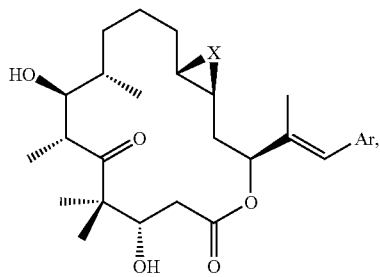
(I-S)

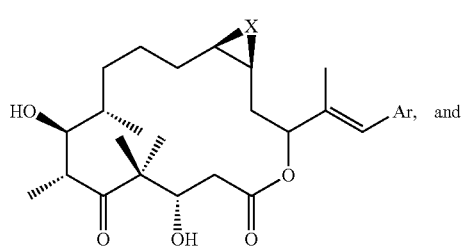
(II)

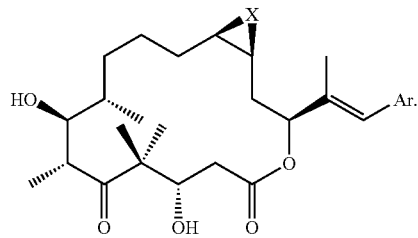
(II-S)

In the above structures, X is a diradical selected from the group consisting of —O—, —C(Y$^1$)(Y$^2$)—, and —C(Y$^1$)(Y$^2$)—C(Y$^1$)(Y$^2$)—. Y$^1$ and Y$^2$ are each radicals independently selected from the group consisting of —H, —F, —Cl and —Br. Ar is a radical represented by the following structure:

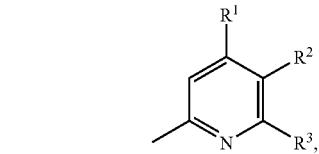

In the above structure, R$^1$ either forms a first fused ring structure with R$^2$ or is a radical selected from —H and a C1-C6 branched or straight chain alkyl represented by —(C(Z$^1$)(Z$^2$)(Z$^3$))$_n$, where $1 \leq n \leq 6$. Z$^1$, Z$^2$, and Z$^3$ are each a radical independently selected from the group consisting of —H, —F, —Cl, —Br, —OH, —NH$_2$, and —(C(Z$^1$)(Z$^2$)(Z$^3$)). However, there is a proviso that, if any one of Z$^1$, Z$^2$, or Z$^3$ is —OH or —NH$_2$, then each of the remaining Z$^1$, Z$^2$, and Z$^3$ is independently selected from the group consisting of —H and —(C(Z$^1$)(Z$^2$)(Z$^3$)). Similarly, R$^2$ either forms the first fused ring structure with R$^1$ or forms a second fused ring structure with R$^3$ or is a radical selected from the group consisting of —H and a C1-C6 branched or straight chain alkyl represented by —(C(Z$^1$)(Z$^2$)(Z$^3$))$_n$, where $1 \leq n \leq 6$. Z$^1$, Z$^2$, and Z$^3$ are as defined above. Similarly, R$^3$ either forms the second fused ring structure with R$^2$ or is a radical selected from the group consisting of —H and a C1-C6 branched or straight chain alkyl represented by —(C(Z$^1$)(Z$^2$)(Z$^3$))$_n$, where $1 \leq n \leq 6$. Again, Z$^1$, Z$^2$, and Z$^3$ are as defined above. The first or second fused ring structure is either an aromatic or heteroaromatic 5- or 6-membered fused ring with or without C1-C6 branched or straight chain alkyl substituents. Preferred species of this aspect of the invention include the following examples:

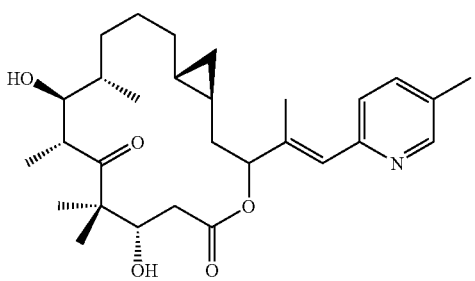

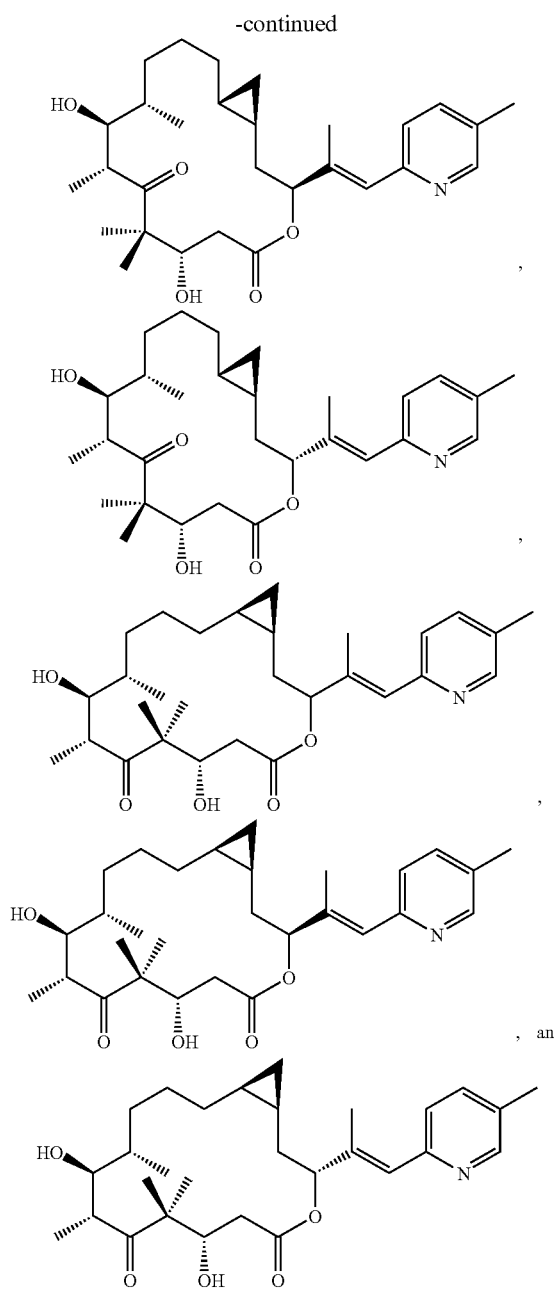

Another aspect of the invention is directed to compounds represented by any of the following structures:

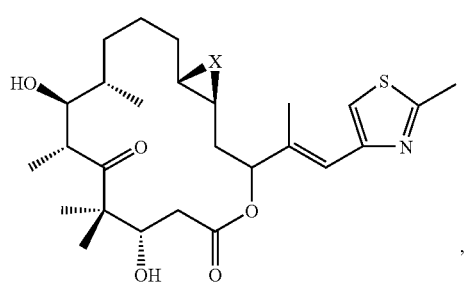

(III)

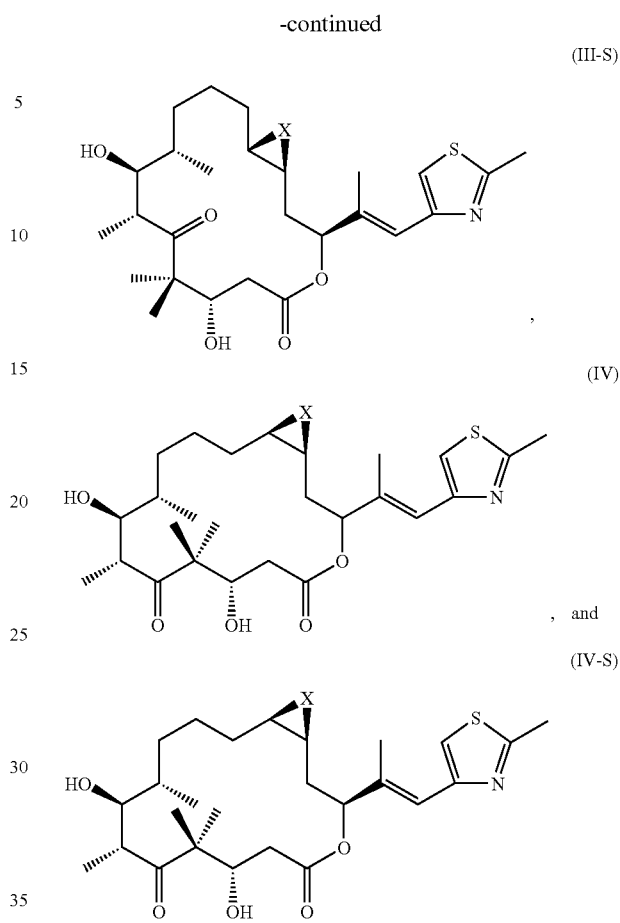

In the above structures, X is a diradical selected from the group consisting of —C(Y$^1$)(Y$^2$)—, and —C(Y$^1$)(Y$^2$)—C(Y$^1$)(Y$^2$)—. Y$^1$ and Y$^2$ are each radicals independently selected from the group consisting of —H, —F, —Cl and —Br. Preferred species of this aspect of the invention include the following examples:

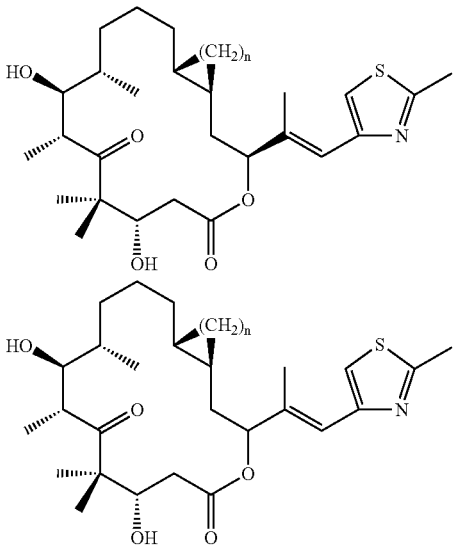

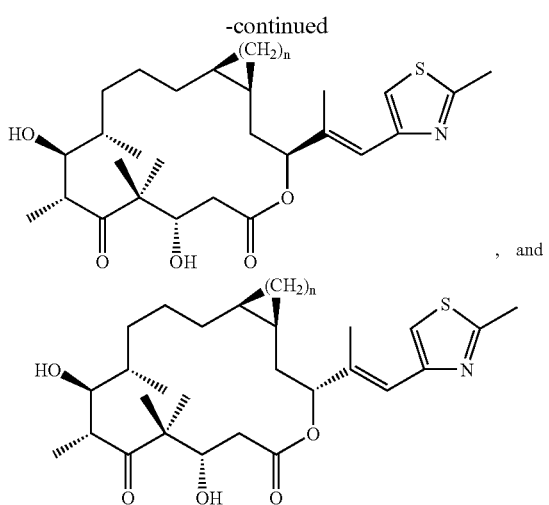
, and

In the above structures, n is either 1 or 2.

Another aspect of the invention is directed to an anticancer reagent comprising any of the compounds described above dissolved or suspended in a physiological solvent suitable for administration to a patient. The compound has a concentration within the physiological solvent sufficient to be cytotoxic to a cancer cell.

Another aspect of the invention is directed to a process for killing a cancer cell comprising the step of contacting the cancer cell with a solution containing a cytotoxic concentration of any compound described above.

Furthermore, the present invention pertains to the use of a compound of formula I, I-S, II, II-S, III, III-S, IV or IV-S or a pharmaceutically acceptable salt or a solvate or a hydrate of such a compound, in a method for the treatment of the human or animal body.

Furthermore, the present invention pertains to the use of a compound of formula I, I-S, II, II-S, III, III-S, IV or IV-S, or a pharmaceutically acceptable salt or a solvate or a hydrate of such a compound, for the preparation of a pharmaceutical product for the treatment of a neoplastic disease.

The term "neoplastic disease" relates in particular to liquid tumor diseases, like leukemia, and solid tumor diseases.

The term "solid tumor disease" especially means breast cancer, ovarian cancer, cancer of the colon and generally the GI tract including gastric cancer, cervix cancer, lung cancer, e.g. small-cell lung cancer and non-small-cell lung cancer, pancreas cancer, renal cancer, glioma, melanoma, head and neck cancer, bladder cancer, thyroid cancer, hepatocellular cancer, prostate cancer and Kaposi's sarcoma.

Moreover, the present invention provides a method for the treatment of a neoplastic disease, which comprises administering a compound of formula I, I-S, II, II-S, III, III-S, IV or IV-S, or a pharmaceutically acceptable salt or a solvate or a hydrate of such a compound, in a quantity effective against said disease, to a warm-blooded animal requiring such treatment.

Furthermore, the present invention relates to a pharmaceutical preparation, comprising a compound of formula I, I-S, II, II-S, III, III-S, IV or IV-S, or a pharmaceutically acceptable salt or a solvate or a hydrate of such a compound, and at least one pharmaceutically acceptable carrier that are suitable for topical, enteral, for example oral or rectal, or parenteral administration and that may be inorganic or organic, solid or liquid. There are used for oral administration especially tablets or gelatin capsules that comprise the active ingredient together with diluents, for example lactose, dextrose, mannitol, and/or glycerol, and/or lubricants and/or polyethylene glycol. Tablets may also comprise binders, for example magnesium aluminum silicate, starches, such as corn, wheat or rice starch, gelatin, methylcellulose, sodium carboxymethylcellulose and/or polyvinylpyrrolidone, and, if desired, disintegrators, for example starches, agar, alginic acid or a salt thereof, such as sodium alginate, and/or effervescent mixtures, or adsorbents, dyes, flavorings and sweeteners. It is also possible to use the pharmacologically active compounds of the present invention in the form of parenterally administrable compositions or in the form of infusion solutions. The pharmaceutical compositions may be sterilized and/or may comprise excipients, for example preservatives, stabilisers, wetting agents and/or emulsifiers, solubilisers, salts for regulating the osmotic pressure and/or buffers. The present pharmaceutical compositions, which may, if desired, comprise other pharmacologically active substances are prepared in a manner known per se, for example by means of conventional mixing, granulating, confectioning, dissolving or lyophilizing processes, and comprise approximately from 1% to 95%, especially from approximately 1% to approximately 20%, active ingredient(s).

The dosage of the active ingredient depends upon a variety of factors including type, species, age, weight, sex and medical condition of the patient; the severity of the condition to be treated; the route of administration; the renal and hepatic function of the patient; and the particular compound employed. A physician, clinician or veterinarian of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug.

The compounds of the present invention can be administered alone or in combination with one or more other therapeutic agents, possible combination therapy taking the form of fixed combinations or the administration of a compound of the invention and one or more other therapeutic agents being staggered or given independently of one another, or the combined administration of fixed combinations and one or more other therapeutic agents. In particular, compounds of the present invention can be administered for example in the case of tumor therapy in combination with chemotherapy, radiotherapy, immunotherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Therapeutic agents for possible combination are especially one or more antiproliferative, cytostatic or cytotoxic compounds, for example a chemotherapeutic agent or several agents selected from the group which includes, but is not limited to, an inhibitor of polyamine biosynthesis, an inhibitor of a protein kinase, especially of a serine/threonine protein kinase, such as protein kinase C, or of a tyrosine protein kinase, such as the EGF receptor tyrosine kinase, e.g. PKI166, the VEGF receptor tyrosine kinase, e.g. PTK787, or the PDGF receptor tyrosine kinase, e.g. STI571, a cytokine, a negative growth regulator, such as TGF-β or IFN-β, an aromatase inhibitor, e.g. letrozole or anastrozole, an inhibitor of the interaction of an SH2 domain with a phosphorylated protein, antiestrogens, topoisomerase I inhibitors, such as irinotecan, topoisomerase II inhibitors, microtubule active agents, e.g. paclitaxel, discodermolide or an epothilone, alkylating agents, antineoplastic antimetabolites, such as gemcitabine or capecitabine, platin compounds, such as carboplatin or cisplatin, anti-angiogenic compounds, gonadorelin agonists, anti-androgens, bisphosphonates, e.g. AREDIA® or ZOMETA®, and trastuzumab. The structure of the active agents identified by code nos., generic or trade names may be taken from the actual edition of the standard compendium "The Merck Index" or from databases, e.g. Patents International (e.g. IMS World Publications). The corresponding content thereof is hereby incorporated by reference.

Another aspect of the invention is a process for synthesizing any of the compounds described above or intermediates thereof, as described in the specification, in particular (a) a process for the preparation of a compound of formula I, wherein X is a diradical selected from the group consisting of —O—, —C($Y^1$)($Y^2$)—, and —C($Y^1$)($Y^2$)—C($Y^1$)($Y^2$)—, $Y^1$ and $Y^2$ are each radicals independently selected from the group consisting of —H, —F, —Cl and —Br; and Ar is a radical represented by the following structure:

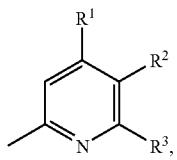

wherein $R^1$ either forms a first fused ring structure with $R^2$ or is a radical selected from —H and a C1-C6 branched or straight chain alkyl represented by —(C($Z^1$)($Z^2$)($Z^3$))$_n$, where $1 \leq n \leq 6$ and $Z^1$, $Z^2$, and $Z^3$ are each a radical independently selected from the group consisting of —H, —F, —Cl, —Br, —OH, —NH$_2$, and —(C($Z^1$)($Z^2$)($Z^3$)), with a proviso that, if any one of $Z^1$, $Z^2$, or $Z^3$ is —OH or —NH$_2$, then each of the remaining $Z^1$, $Z^2$, and $Z^3$ is independently selected from the group consisting of —H and —(C($Z^1$)($Z^2$)($Z^3$));

$R^2$ either forms the first fused ring structure with $R^1$ or forms a second fused ring structure with $R^3$ or is a radical selected from the group consisting of —H and a C1-C6 branched or straight chain alkyl represented by —(C($Z^1$)($Z^2$)($Z^3$))$_n$, where $1 \leq n \leq 6$ and $Z^1$, $Z^2$, and $Z^3$ are each a radical independently selected from the group consisting of —H, —F, —Cl, —Br, —OH, —NH$_2$, and —(C($Z^1$)($Z^2$)($Z^3$)), with a proviso that, if any one of $Z^1$, $Z^2$, or $Z^3$ is —OH or —NH$_2$, then each of the remaining $Z^1$, $Z^2$, and $Z^3$ is independently selected from the group consisting of —H and —(C($Z^1$)($Z^2$)($Z^3$));

$R^3$ either forms said second fused ring structure with $R^2$ or is a radical selected from the group consisting of —H and a C1-C6 branched or straight chain alkyl represented by —(C($Z^1$)($Z^2$)($Z^3$))$_n$, where $1 \leq n \leq 6$ and $Z^1$, $Z^2$, and $Z^3$ are each a radical independently selected from the group consisting of —H, —F, —Cl, —Br, —OH, —NH$_2$, and —(C($Z^1$)($Z^2$)($Z^3$)), with a proviso that, if any one of $Z^1$, $Z^2$, or $Z^3$ is —OH or —NH$_2$, then each of the remaining $Z^1$, $Z^2$, and $Z^3$ is independently selected from the group consisting of —H and —(C($Z^1$)($Z^2$)($Z^3$)); said first or second fused ring structure is either an aromatic or heteroaromatic 5- or 6-membered fused ring with or without C1-C6 branched or straight chain alkyl substituents; and the stereogenic center in 15-position can have R or S configuration, wherein a compound of the formula V

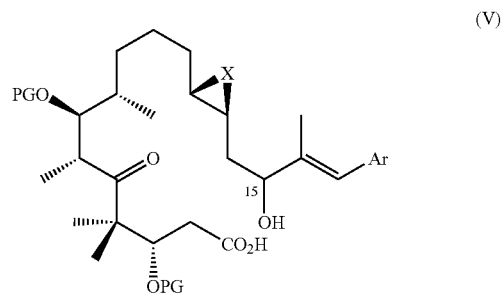

wherein X and Ar have the meaning as defined above for a compound of formula I and PG is a protecting group for a hydroxy function, in a first step is condensed by a esterification reaction, optionally in the presence of a catalyst, and in a second step the protecting group is detached thus furnishing a lactone of formula I; and (b) a process for the preparation of a compound of formula III, wherein X is a diradical selected from the group consisting of —C($Y^1$)($Y^2$)—, and —C($Y^1$)($Y^2$)—C($Y^1$)($Y^2$)—, and $Y^1$ and $Y^2$ are each radicals independently selected from the group consisting of —H, —F, —Cl and —Br and the stereogenic center in 15-position can have R or S configuration, wherein a compound of the formula VI

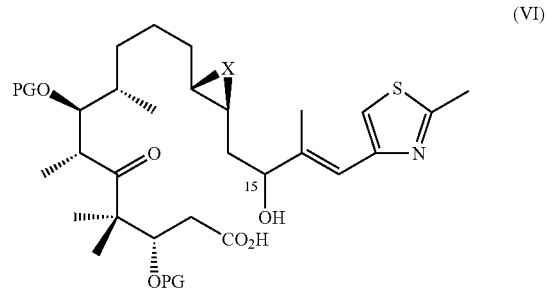

wherein X has the meaning as defined above for a compound of formula III and PG is a protecting group for a hydroxy function, in a first step is condensed by a esterification reaction, optionally in the presence of a catalyst, and in a second step the protecting group is detached thus furnishing a lactone of formula III.

BRIEF DESCRIPTION OF FIGURES

FIG. 1 illustrates the structure of the epothilones and preferred epothilone analogs.

FIG. 15 illustrates a table that displays the cytotoxicity of epothilones 1 through 12 and paclitaxel against 1A9 human ovarian carcinoma cells and β-tubulin mutant cell lines selected with paclitaxel or epothilone A.

FIG. 16 illustrates a table of tubulin polymerization potency and cytotoxicity of epothilones 1 through 12 and paclitaxel against human epidermoid cancer cell lines.

CHEMICAL SYNTHESIS

Figure 2:
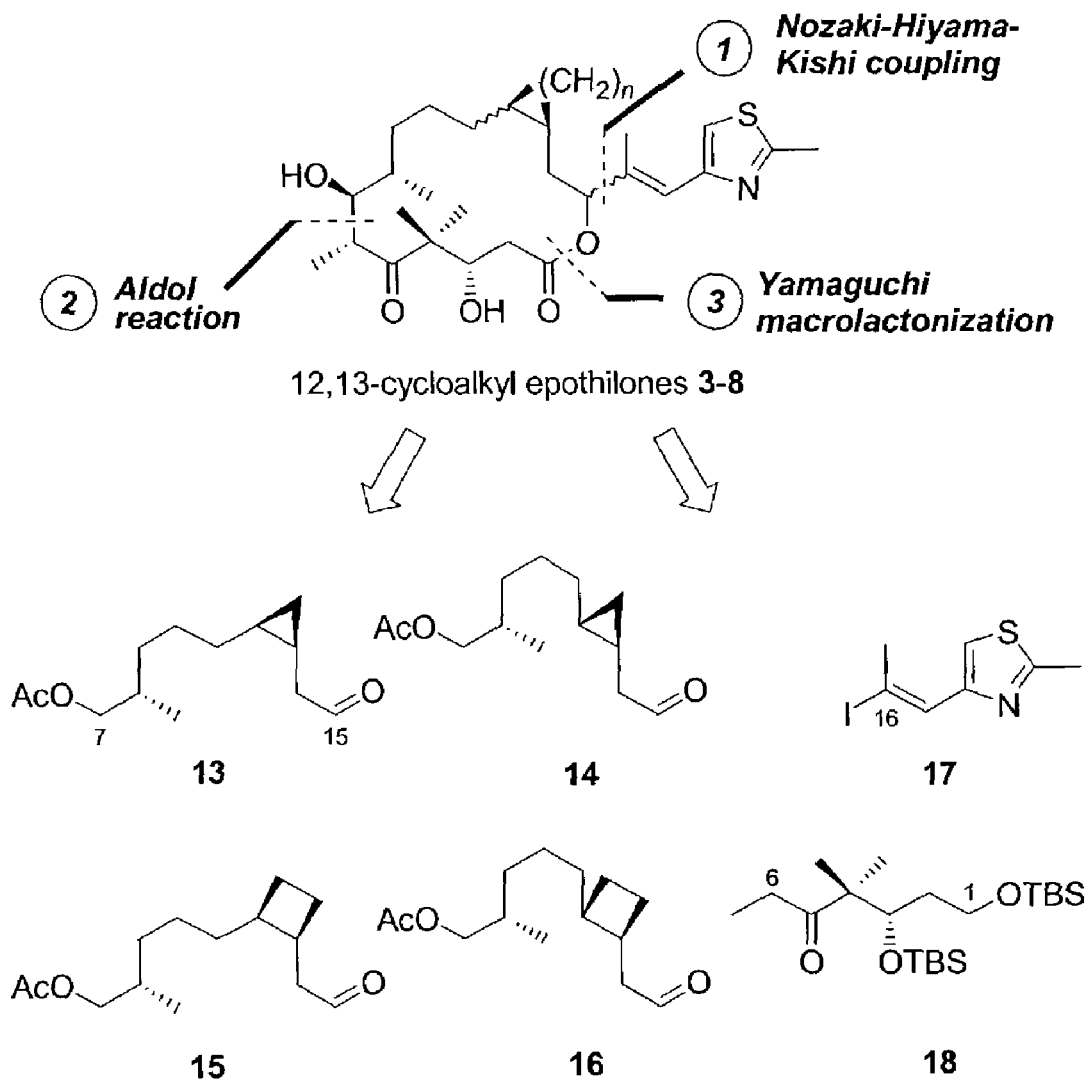
FIG. 2 illustrates the retrosynthetic analysis used for the chemical synthesis of the designed 12,13-cycloalkane thiazole epothilone analogs 3-8.

Thiazole Epothilone Analogs. The chemical synthesis of the designed 12,13-cycloalkane thiazole epothilone analogs 3-8 was carried out according to a strategy derived from the retrosynthetic analysis shown in Scheme 1. Thus, Nozaki-Hiyama-Kishi coupling (Takai, K.; et al. *Tetrahedron Lett.* 1983, 24, 5281-5284; Jin, H.; et al. *J. Am. Chem. Soc.* 1986, 108, 5644-5646), an aldol reaction and a Yamaguchi lactonization (Inanaga, J.; et al. *Bull. Chem. Soc. Jpn.* 1979, 52, 1989-1993; Mulzer, J.; et al. *Synthesis* 1992, 215-228; Nicolaou, K. C.; et al. *Chem. Eur. J.* 2000, 6, 2783-2800; Nicolaou, K. C.; et al. *J. Am. Chem. Soc.* 1997, 119, 7974-7991) were employed to disconnect the three strategic bonds as indicated, revealing building blocks 13-16, 17 and 18. The assembly and elaboration of these building blocks to the final targets was to follow the order shown in Scheme 1. Thus, coupling of the C7-C15 aldehyde fragment with the heterocyclic vinyl iodide, followed by elaboration and aldol reaction with the C1-C6 ketone segment would lead, upon further elaboration, to the desired seco-hydroxy acid. Cyclization according to our Yamaguchi strategy (Inanaga, J.; et al. *Bull. Chem. Soc. Jpn.* 1979, 52, 1989-1993; Mulzer, J.; et al. *Synthesis* 1992, 215-228; Nicolaou, K. C.; et al. *Chem. Eur. J.* 2000, 6, 2783-2800; Nicolaou, K. C.; et al. *J. Am. Chem. Soc.* 1997, 119, 7974-7991) would then furnish, upon deprotection, the desired epothilone analogs.

The required building blocks 13-17 were synthesized as shown in Schemes 2-5, while ketone 18 was prepared by the previously described route (Nicolaou, K. C.; et al. *J. Am. Chem. Soc.* 1997, 119, 7974-7991). The first required C7-C15 aldehyde (13) was constructed as shown in Scheme 2. Thus, Swern oxidation of optically active aldehyde 19 (Charette, A. B.; et al. *J. Am. Chem. Soc.* 1998, 120, 11943-11952) was followed by Wittig reaction and acid hydrolysis to afford the homologated aldehyde 20 in 85% overall yield. A second Wittig reaction employing commercially available phosphonium salt 21 led to a mixture of cis and trans olefins 22 (cis:trans ca. 20:1, 78% yield) which was reduced with diimide (Pasto, D. J.; Taylor, R. T. *Org. React.* 1991, 40, 92-155) to the saturated alcohol 23 (94% yield). Acetylation of the free hydroxyl group in 23 (100% yield) yielded acetate 24, which upon hydrogenolysis of the benzyl ether afforded alcohol 25 (78% yield). Direct hydrogenation of 22 with palladium catalysts in order to simultaneously reduce the double bond and cleave the benzyl ether proved impractical, due to significant amounts of cyclopropyl ring-opened by-products. Furthermore, although platinum catalysts cleanly reduced the double bond in 22, they also reduced the aromatic ring of the benzyl group, rather than effecting hydrogenolysis of the C—O bond. Alcohol 25 was oxidized to the corresponding aldehyde (89% yield) with TPAP-NMO (for abbreviations of reagents and protecting groups, see legends in schemes), and then homologated to the desired aldehyde 13 via enol ether 26 by the two-step procedure described above for 20 (Wittig reaction followed by acidic hydrolysis), in 50% overall yield.

Shown in Scheme 3 is the synthesis of the trans-cyclopropyl aldehyde 14, which closely parallels that of its cis counterpart 13 described above. Thus, a Charette cyclopropanation (Charette, A. B.; et al. *J. Am. Chem. Soc.* 1998, 120, 11943-11952) of allylic alcohol 27 (Azzena, F.; et al. *Tetrahedron* 1995, 51, 10601-10626; Trost, B. M.; Verhoeven, T. R. *J. Am. Chem. Soc.* 1980, 102, 4743-4763) yielded the enantiomerically enriched cyclopropane 29 in 98% yield (ee >90% by Mosher ester analysis) (Dale, J. A.; Dull, D. L.; Mosher, H. S. *J. Org. Chem.* 1969, 34, 2543-2549; Dale, J. A.; Mosher, H. S. *J. Am. Chem. Soc.* 1973, 95, 512-519). Oxidation ($SO_3$·py) followed by Wittig reaction afforded enol ether 30 (81% overall yield), whose desilylation (TBAF), benzylation (NaH, BnBr) and acid hydrolysis led to the homologated aldehyde, which reacted with the ylid derived from phosphonium salt 21 to afford olefin 31 in 58% yield for the five steps. Diimide reduction, acetylation and hydrogenolysis furnished alcohol 32 (98% overall yield). Dess-Martin oxidation then yielded the desired aldehyde 14, which was not isolated, but rather used immediately for the subsequent Nozaki-Hiyama-Kishi coupling (vide infra).

The syntheses of the C12-C13-cyclobutyl aldehydes 15 and 16 were carried out as shown in Scheme 4. As these compounds are very closely related to the cyclopropane derivatives 13 and 14, a similar synthetic route was again followed. Thus, starting from the monoacetate 33, readily available through enzymatic group-selective saponification of the corresponding diacetate (Laumen, K.; Schneider, M. *Tetrahedron Lett.* 1985, 26, 2073-2076; Kasel, W.; et al. *J. Chem. Soc., Chem. Commun.* 1985, 1563-1564), cis-aldehyde 34 was prepared by Dess-Martin periodinane oxidation (95% yield), while the corresponding trans-aldehyde 39 was conveniently available by base-catalyzed epimerization of 34 (88% from 33). Following the route described for the cyclopropyl derivatives, 34 and 39 were homologated to 35 and 40, respectively, and the latter compounds were coupled with the chiral phosphorane derived from enantiomerically pure phosphonium salt 21 and NaHMDS-TMSCl to yield olefins 36 and 41, respectively. Hydrogenation of the double bond using a platinum catalyst, followed by standard protecting group manipulations, afforded alcohols 38 and 43, which were again homologated and protected, as summarized in Scheme 4, thus producing aldehydes 15 and 16, respectively.

The requisite vinyl iodide 17 was constructed from aldehyde 44[7] via a sequence involving (i) a modified Corey-Fuchs protocol (Grandjean, D.; et al. *Tetrahedron Lett.* 1994, 35, 3529-3530) with in situ methylation of the intermediate acetylenide via intermediates 45 (88%) and 46 (97%); (ii) stereoselective hydrostannylation (Betzer, J. -F.; et al. *Tetrahedron Lett.* 1997, 38, 2279-2282) (84%); and (iii) iodine-tin exchange (99%), as shown in Scheme 5. This sequence represents a significant improvement, both regarding simplicity and yields, over the preliminary route previously disclosed (Nicolaou, K. C.; et al. *ChemBioChem* 2001, 1, 69-75).

With all the building blocks in hand, final assembly of epothilone analogs 3-8 could begin. The cyclopropyl analogs 3, 5 and 7 were synthesized as shown in Scheme 6. Aldehyde 13 was coupled with vinyl iodide 17 by the Nozaki-Hiyama-Kishi procedure employing $CrCl_2$—$NiCl_2$ (Takai, K.; et al. *Tetrahedron Lett.* 1983, 24, 5281-5284; Jin, H.; et al. *J. Am. Chem. Soc.* 1986, 108, 5644-5646), furnishing a diastereomeric mixture of alcohols 48 (ca. 1:1 ratio, 56% yield, unoptimized). This mixture was taken through the sequence until chromatographic separation of the two isomers became feasible upon Yamaguchi macrolactonization (vide infra) (Inanaga, J.; et al. *Bull. Chem. Soc. Jpn.* 1979, 52, 1989-1993; Mulzer, J.; et al. *Synthesis* 1992, 215-228; Nicolaou, K. C.; et al. *Chem. Eur. J.* 2000, 6, 2783-2800). Silylation of 48 (TBSOTf-2,6-lutidine, 100% yield) furnished silyl ether 49 which was deacetylated (DIBAL, 99% yield) to yield the advanced intermediate alcohol 50. In a similar way, trans-aldehyde 14 was coupled with iodide 17, but this time, oxidation (DMP) of the resulting mixture of epimeric secondary alcohols led to ketone 56 in 75% overall yield. Stereoselective reduction of 56 using (–)-DIPCI (Brown, H. C.; Ramachandran, P. V. *Acc. Chem. Res.* 1992, 25, 16-24; Brown, H. C.; et al. *J. Org. Chem.* 1987, 52, 5406-5412) afforded alcohol 57 as a single stereoisomer (by $^1$H NMR spectroscopy) in 84% yield, thus demonstrating the flexibility of this route to generate either one, or both, C15 epimers. The 15S stereochemistry was assumed based on the chirality of the reducing agent. Compound 57 was protected as a TBS ether (58, TBSOTf, 2,6-lut., 91% yield) which was then deacetylated with DIBAL to provide the desired alcohol 59 in 93% yield. The stage was now set for the stereoselective aldol coupling which was employed to simultaneously create the C6-C7 bond and set the stereochemistry at these stereocenters. To this end, DMP oxidation of 50 and 59, respectively, was immediately followed by aldol addition of the previously described C1-C6 ketone 18 (Nicolaou, K. C.; et al. *J. Am. Chem. Soc.* 1997, 119, 7974-7991) using LDA according to our optimized protocol (Nicolaou, K. C.; et al. *Chem. Eur. J.* 2000, 6, 2783-2800). In this manner, aldols 51 (63%) and 60 (70%) were generated and isolated with complete control of the C6-C7 stereochemistry (as determined by $^1$H NMR spectroscopy). Protection of the secondary hydroxyl groups as the TBS ethers 52 and 61, followed by a two-step oxidation of the C1 position (liberated selectively by the action of HF.py) and selective cleavage of the C15 TBS ether (TBAF), afforded the hydroxy acids 53 and 62, respectively. Yamaguchi macrolactonization (Inanaga, J.; et al. *Bull. Chem. Soc. Jpn.* 1979, 52, 1989-1993; Mulzer, J.; et al. *Synthesis* 1992, 215-228; Nicolaou, K. C.; et al. *Chem. Eur. J.* 2000, 6, 2783-2800) of 53 gave a 69% combined yield of the protected epothilone derivatives 54 and 55, which were chromatographically separated [54 (42%); 55 (27%)]. Analogously, macrolactonization of 62 yielded bis-silyl ether 63 (53% from 61 after 5 steps). Desilylation of 54, 55 and 63 with 20% TFA in $CH_2Cl_2$ finally afforded the desired epothilone analogs 3, 5 and 7, respectively. The 15S configuration of the trans analog 7 was now further corroborated by comparison of the $^1$H NMR spectrum of 7 with those of the cis isomers 3 and 5, where the spectrum of 7 is more similar to that of 3 than to that of 5, particularly considering the signals from the protons attached to C2 and C15, see Supporting Information.

The cis-cyclobutyl thiazole epothilones 4 and 6 were assembled in an analogous fashion, as summarized in Scheme 7. A Nozaki-Hiyama-Kishi coupling between cis-aldehyde 15 and the side chain vinyl iodide 17 afforded the secondary alcohol 64 (89% yield) as a 1:1 mixture of C15 epimers. Protective group manipulations and oxidation yielded, via intermediates 65 and 66, aldehyde 67, which smoothly underwent the stereoselective aldol coupling reaction with ketone 18, thus producing alcohol 68. Further manipulation of protecting groups and oxidation of the C1 position yielded hydroxy acid 72, which was cyclized by applying the Yamaguchi protocol to afford the two lactones 73 and 74. At this point, the C15 epimers 73 and 74 were chromatographically separated and deprotected to yield the desired cis-cyclobutyl epothilones 4 and 6 respectively, and in good overall yields.

The trans-cyclobutyl thiazole epothilone 8 was prepared by a similar sequence, as detailed in Scheme 8. Thus, after the Nozaki-Hiyama-Kishi coupling between aldehyde 16 and iodide 17, the resulting alcohol was oxidized to the corresponding enone 75, which was then stereoselectively reduced with (–)-DIPCI (Brown, H. C.; Ramachandran, P. V. *Acc. Chem. Res.* 1992, 25, 16-24; Brown, H. C.; et al. *J. Org. Chem.* 1987, 52, 5406-5412) to afford only the (15S)-epimer 76. The remaining steps followed the same sequence described for the cis compounds (see Scheme 7), and proceeded smoothly and in similar yields, affording the targeted trans-cyclobutyl epothilone 8.

Pyridine Epothilone Analogs. Some of the most active epothilone analogs prepared to date include within their structures a pyridine side chain as a replacement for the thiazole moiety of the naturally occurring substances (Nicolaou, K. C.; et al. *Chem. Biol.* 2000, 7, 593-599). Given the very promising preliminary results with cyclopropane epothilone analog 3, we reasoned that combining these two structural modifications might result in highly active compounds despite the absence of the epoxide oxygen. Such compounds (e.g. 9-12, FIG. 1) may be metabolically more stable leading to longer in vivo lifetime and lower toxicity. In an effort to improve the overall synthesis of these compounds, and in order to accommodate future preparation of other side chain-modified analogs via a convergent strategy, a slightly different scheme for their total synthesis was designed based on the retrosynthetic analysis shown in Scheme 9. The devised strategy for the construction of the pyridine cycloalkane epothilones (9-12) is similar to that utilized for the total synthesis of their thiazole counterparts except for the reversal of the coupling order of the fragments. Thus, the aldol reaction of building blocks 84 and 85 with ketone 18 will now precede the Nozaki-Hiyama-Kishi coupling with vinyl iodide 86.

The required building blocks 85 and 86 were prepared as shown in Scheme 10. A Wittig reaction between the ylid derived from the enantiomerically pure phosphonium salt 21 and NaHMDS-TMSCI, and the commercially available aldehyde 87 (68% yield), followed by protection of the resulting alcohol 88 as its TBDPS ether (TBDPSCI-imid.), afforded alkene 89 in 89% yield. Hydrogenation of the double bond in 89 with concomitant cleavage of the benzyl ether gave primary alcohol 90 in 75% yield. This compound (90) was then converted into the corresponding iodide (91) in 93% yield by exposure to $I_2/PPh_3$. Coupling of 92 with alkyne 92 (n-BuLi, 72% yield), followed by removal of the TBS group (BF$_3$.OEt$_2$) from the resulting alkyne 93, produced the propargylic alcohol 94 (89% yield). This compound was used as a common precursor to prepare both the cis- and the trans-cyclopropyl pyridine epothilone analogs (9-12). The synthesis of the cis series of compounds commenced with a nickel boride reduction (Taber, D. F.; et al. *J. Org. Chem.* 1997, 62, 194-198) of alkyne 94 to furnish cis olefin 95 in 95% yield (Scheme 10), while the corresponding trans alkene (97) was prepared from the same intermediate (94) via reduction with LiAlH$_3$(OMe) (Ashby, E. C.; et al. *J. Am. Chem. Soc.* 1975, 97, 3158-3162) (83% yield). Charette cyclopropanation (Charette, A. B.; et al. *J. Am. Chem. Soc.* 1998, 120, 11943-11952) of 95 and 97 smoothly afforded the cyclopropanes 96 (99% yield) and 98 (93%) in >95% de, as judged by $^1$H NMR spectroscopic analysis of the corresponding Mosher esters (Dale, J. A.; Dull, D. L.; Mosher, H. S. *J. Org. Chem.* 1969, 34, 2543-2549; Dale, J. A.; Mosher, H. S. *J. Am. Chem. Soc.* 1973, 95, 512-519). Subsequent benzylation of the primary hydroxyl group, followed by removal of the silyl group at the other end of the molecule led to the desired primary alcohols 85 and 86, respectively.

The requisite side chain vinyl iodide 87 was synthesized as shown in Scheme 11. A Sonogashira coupling of 5-methyl-2-bromopyridine 99 with propyne (Arcadi, A.; et al. *Tetrahedron* 1994, 50, 437-452) yielded alkyne 100 in 98% yield. This was then hydrostannylated, and the tin was exchanged for iodine (86% for two steps) by the same method as that employed to prepare the thiazole side chain precursor 17 (Scheme 5), thus yielding iodide 87 via stannane 101 (100% yield).

The final stages of the synthesis of the targeted pyridine analogs are depicted in Schemes 12 and 13. Oxidation of alcohols 85 and 86 with Dess-Martin periodinane was followed by the stereoselective aldol coupling with ketone 18 (Nicolaou, K. C.; et al. *J. Am. Chem. Soc.* 1997, 119, 7974-7991) previously employed (vide supra). This coupling was performed according to our general procedure (Nicolaou, K. C.; et al. *Chem. Eur. J.* 2000, 6, 2783-2800), yielding aldols 102 (75% yield) and 108 (89% yield) with a dr of ca. 10:1 (by $^1$H NMR spectroscopy) in both cases. Further elaboration of these compounds (102 and 108) involved TBS protection of their secondary alcohols, selective removal of the primary TBS group (HF.py), oxidation of the resulting primary alcohol (DMP; NaClO$_2$), and methylation of the so obtained carboxylic acid, leading to compounds 104 and 110, as shown in Scheme 12. Hydrogenolysis of the benzyl ether from 104 and 110 was followed by oxidation of the resulting primary alcohols (105 and 111) to the corresponding aldehydes (DMP) and homologation to install the C15 carbon atom, thus yielding aldehydes 107 and 113 via enol ethers 106 and 112, respectively.

The cis-aldehyde 107 was then subjected to the Nozaki-Hiyama-Kishi coupling with vinyl iodide 87 to yield methyl ester 114 (43%, unoptimized), which was hydrolyzed to the corresponding acid (115) in 76% yield (Scheme 13). The ester hydrolysis (114→115) was extremely slow, requiring 4 days for completion. When the same sequence was applied to the trans compound 113, it proved impossible to hydrolyze the corresponding methyl ester at a practical rate after the Nozaki-Hiyama-Kishi coupling. Clearly, another protecting group was needed for the C1 carboxylic acid, and we opted to try a trimethylsilylethyl (TMSE) ester instead of the methyl ester. In the event, the aldehyde 113 was reduced to the hydroxy ester 118 (NaBH$_4$, 72% yield), which could now be hydrolyzed to the corresponding hydroxy acid and protected (TMSE-OH, EDC, 4-DMAP), affording the TMSE ester 119 in 81% yield. Direct hydrolysis of aldehyde 113 was unsuccessful, which dictated the adoption of the above plan requiring reduction to the alcohol prior to hydrolysis. Reoxidation of 119 with Dess-Martin periodinane gave aldehyde 120 (93% yield), which smoothly underwent the Nozaki-Hiyama-Kishi coupling with 87 to furnish hydroxy ester 121 in 71% yield. Cleavage of the TMSE ester with TBAF now proceeded smoothly, affording hydroxy acid 122 in high yield. Both the cis and trans isomers 115 and 122 were cyclized using the Yamaguchi protocol (Inanaga, J.; et al. *Bull. Chem. Soc. Jpn.* 1979, 52, 1989-1993; Mulzer, J.; et al. *Synthesis* 1992, 215-228; Nicolaou, K. C.; et al. *Chem. Eur. J.* 2000, 6, 2783-2800) (70% yield), after which the C15 epimers were chromatographically separated, yielding compounds 116, 117, 123 and 124. Desilylation of these compounds finally afforded the desired cyclopropyl epothilones 9-12 in excellent yields.

The starting materials used herein are commercially available or can be prepared in a manner known per se.

In FIGS. 10, 11, 13 and 14 the preparation of a compound of formula I or II is described wherein X is CH$_2$ and Ar is a radical represented by the following structure:

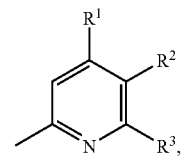

wherein R$_1$ and R$_3$ are H and R$_2$ is methyl.

Compounds of formula I, wherein in said radical R$^1$ either forms a first fused ring structure with R$^2$ or is a radical selected from —H and a C1-C6 branched or straight chain alkyl represented by —(C(Z$^1$)(Z$^2$)(Z$^3$))$_n$, where $1 \leq n \leq 6$ and Z$^1$, Z$^2$, and Z$^3$ are each a radical independently selected from the group consisting of —H, —F, —Cl, —Br, —OH, —NH$_2$, and —(C(Z$^1$)(Z$^2$)(Z$^3$)), with a proviso that, if any one of Z$^1$, Z$^2$, or Z$^3$ is —OH or —NH$_2$, then each of the remaining Z$^1$, Z$^2$, and Z$^3$ is independently selected from the group consisting of —H an —(C(Z$^1$)(Z$^2$)(Z$^3$));

R$^2$ either forms the first fused ring structure with R$^1$ or forms a second fused ring structure with R$^3$ or is a radical selected from the group consisting of —H and a C1-C6 branched or straight chain alkyl represented by —(C(Z$^1$)(Z$^2$)(Z$^3$))$_n$, where $1 \leq n \leq 6$ and Z$^1$, Z$^2$, and Z$^3$ are each a radical independently selected from the group consisting of —H, —F, —Cl, —Br, —OH, —NH$_2$, and —(C(Z$^1$)(Z$^2$)(Z$^3$)), with a proviso that, if any one of Z$^1$, Z$^2$, or Z$^3$ is —OH or —NH$_2$, then each of the remaining Z$^1$, Z$^2$, and Z$^3$ is independently selected from the group consisting of —H and —(C(Z$^1$)(Z$^2$)(Z$^3$));

R$^3$ either forms said second fused ring structure with R$^2$ or is a radical selected from the group consisting of —H and a C1-C6 branched or straight chain alkyl represented by —(C(Z$^1$)(Z$^2$)(Z$^3$))$_n$, where $1 \leq n \leq 6$ and Z$^1$, Z$^2$, and Z$^3$ are each a radical independently selected from the group consisting of —H, —F, —Cl, —Br, —OH, —NH$_2$, and —(C(Z$^1$)(Z$^2$)(Z$^3$)), with a proviso that, if any one of Z$^1$, Z$^2$, or Z$^3$ is —OH or —NH$_2$, then each of the remaining Z$^1$, Z$^2$, and Z$^3$ is independently selected from the group consisting of —H and —(C(Z$^1$)(Z$^2$)(Z$^3$));

said first or second fused ring structure is either an aromatic or heteroaromatic 5- or 6-membered fused ring with or without C1-C6 branched or straight chain alkyl substituents; can be obtained, for example, by first reacting a pyridine derivative of formula VII

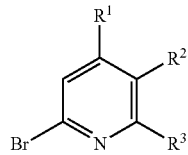

(VII)

wherein $R^1$, $R^2$ and $R^3$ have the meanings as defined above, in a suitable solvent with $HCCCH_3$ in the presence of a Pd(II)-catalyst and copper(I)iodide, furnishing a pyridine derivative of formula VIII,

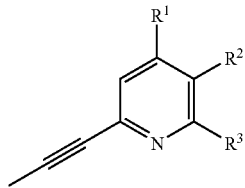

(VIII)

wherein $R^1$, $R^2$ and $R^3$ have the meanings as defined above, hydrostannylating the obtained product of formula VIII in a second step in order to obtain a pyridine derivative of formula IX,

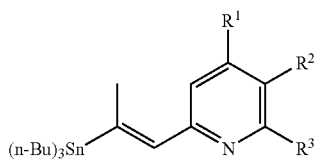

(IX)

wherein $R^1$, $R^2$ and $R^3$ have the meanings as defined above, which pyridine derivative of formula IX is transformed in a third step by the reaction with iodine into the corresponding iodide of formula X

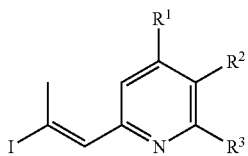

(X)

wherein $R^1$, $R^2$ and $R^3$ have the meanings as defined above. Said iodide of formula X can then be employed in the reaction sequence illustrated in FIG. 14 instead of the compound of number 87.

Figure 9:
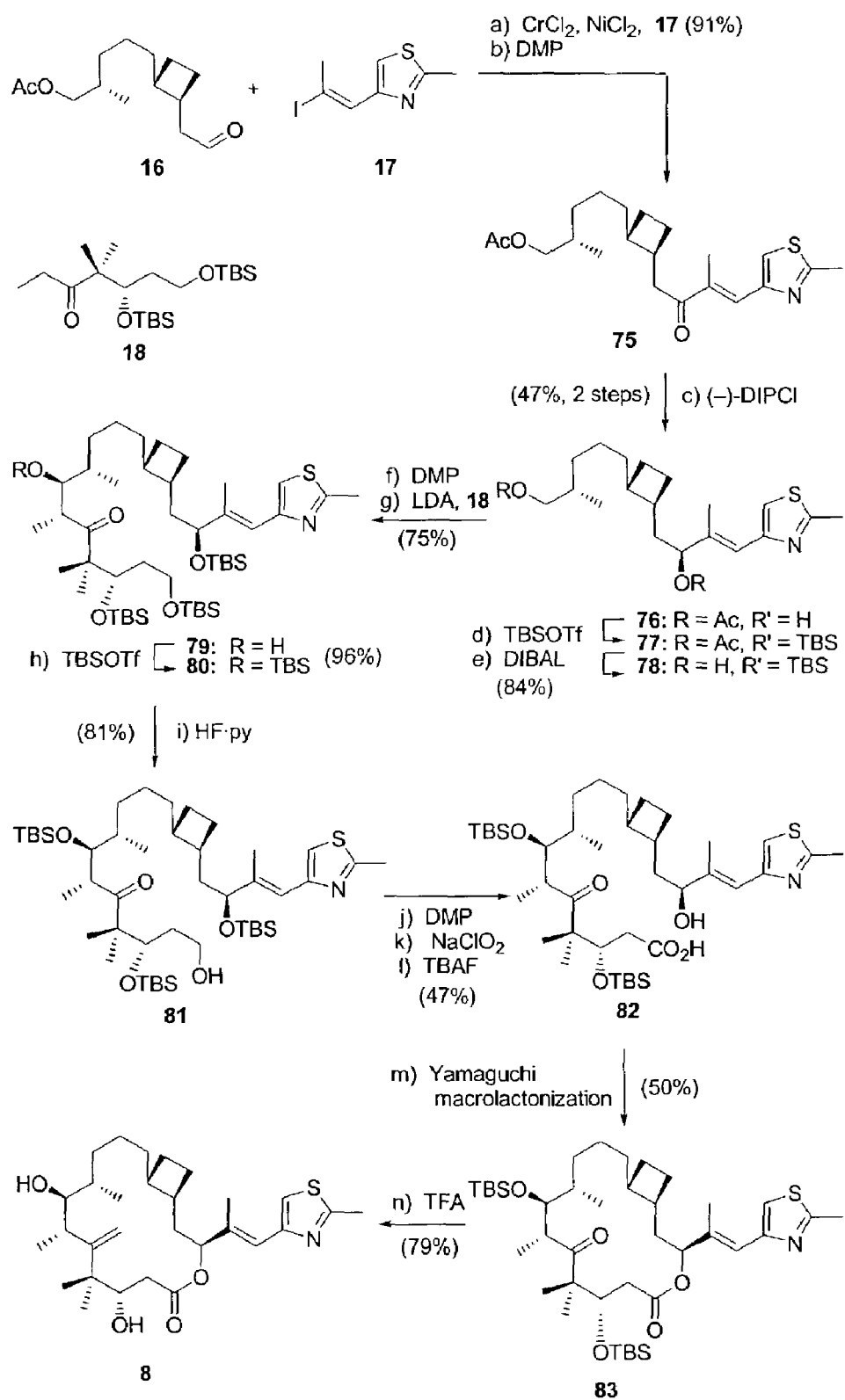
FIG. 9 illustrates a scheme showing the synthesis of the trans-cyclobutyl epothilone analog 8.

Furthermore, said iodide of formula X can, e.g., also be employed in the reaction sequence illustrated in FIG. 9 instead of the iodide of number 17 thus furnishing compounds of formula I, wherein X is a diradical of formula —$CH_2$—$CH_2$— and Ar is a radical represented by the following structure:

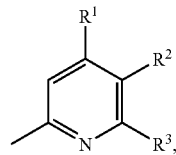

wherein $R^1$, $R_2$ and $R_3$ have the meanings as provided for a compound of formula X.

The term "protecting groups for a hydroxy group" as used herein refers to acid labile protecting groups for a hydroxy group, which groups are known as such. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned hereinabove and hereinafter.

The protection of hydroxy groups by protecting groups, the protecting groups themselves, and their cleavage reactions are described for example in standard reference works, such as J. F. W. McOmie, "Protective Groups in Organic Chemistry", Plenum Press, London and New York 1973, in T. W. Greene, "Protective Groups in Organic Synthesis", Wiley, New York 1981, in "The Peptides"; Volume 3 (editors: E. Gross and J. Meienhofer), Academic Press, London and New York 1981, in "Methoden der organischen Chemie" (*Methods of organic chemistry*), Houben Weyl, 4th edition, Volume 15/I, Georg Thieme Verlag, Stuttgart 1974, in H.-D. Jakubke and H. Jescheit, "Aminosäuren, Peptide, Proteine" (*Amino acids, peptides, proteins*), Verlag Chemie, Weinheim, Deerfield Beach, and Basel 1982, and in Jochen Lehmann, "Chemie der Kohlenhydrate: Monosaccharide und Derivate" (*Chemistry of carbohydrates: monosaccharides and derivatives*), Georg Thieme Verlag, Stuttgart 1974.

Preferred protecting groups are silyl ethers which are acid labile like tert-butyl-dimethyl-silyl (TBS) ether, triethylsilyl (TES) ether, triisopropylsilyl (TIPS) ether, diethylisopropylsilyl (DEIPS) ether, isopropyldimethylsilyl (IPDMS) ether or thexyldimethylsilyl (TDS) ether.

Chemical Biology

The biological activities of the synthesized epothilones were evaluated through cytotoxicity and tubulin polymerization assays. Cytotoxicity was first evaluated in a set of ovarian carcinoma cell lines, including a parental cell line (1A9) and three drug-resistant cell lines, namely the paclitaxel-resistant cell lines (Giannakakou, P.; et al. *J. Biol. Chem.* 1997, 272, 17118-17125) 1A9/PTX10 and 1A9/PTX22 and the epothilone-resistant cell line (Giannakakou, P.; et al. *Proc. Natl. Acad. Sci. USA* 2000, 97, 2904-2909) 1A9/A8. These resistant cell lines harbor distinct acquired P-tubulin mutations which affect drug-tubulin interaction and result in impaired taxane and epothilone-driven tubulin polymerization. The results of these biological investigations are summarized in Table 1. Further cytotoxicity studies were undertaken using a set of human epidermoid cancer cell lines, including a parent cell line (KB-31), and a paclitaxel-resistant (due to P-gp overexpression) cell line (KB-8511). The results of these studies are summarized in Table 2.

In agreement with previous reports (Nicolaou, K. C.; et al. *ChemBioChem* 2001, 1, 69-75; Johnson, J.; et al. *Org. Lett.* 2000, 2, 1537-1540), we found that the cyclopropyl epothilone A (3) inhibits slightly more potently the 1A9 and KB-31 cell growth than the parent compound epothilone A (1). The 15S-cyclobutyl epothilone A (4) retains good activity but is less potent than either 1 or 3. It is noteworthy that the 15R-isomers (5 and 6) of both compounds are inactive at low concentrations against the parental sensitive 1A9 and KB-31 cells. Interestingly, even the (12R,13S)-trans-substituted epothilones 7 and 8 showed good activity, again with the cyclopropyl analog being the most potent. These results are in agreement with our previous report concerning trans-epoxide analogs of epothilones A and B (Nicolaou, K. C.; et al. *Angew. Chem. Int. Ed. Engl.* 1997, 36, 2097-2103). In another study (Nicolaou, K. C.; et al. *Chem. Biol.* 1998, 5, 365-372), we found that (13R)-cyclopropyl epothilones 125 and 126 (see FIG. 2), originally incorrectly assigned as (13S)-diastereomers, were inactive. Thus, we have now prepared and tested all four possible diastereomers of 12,13-cyclopropyl epothilone A, and on the basis of these results, it would appear that while the configuration at C12 has relatively little influence on the cytotoxicity, the 13S configuration is essential.

Remarkably, the trans-cyclopropyl pyridine analog 11 showed outstanding activity against all of our cell lines, with $IC_{50}$=0.6 nM in the 1A9 human ovarian carcinoma cell line. The cis analog 9 was also highly active, but was a factor of three to five less active than 11. Again, the 15R isomeric analogs (10 and 12) were inactive.

It is noteworthy that the active compounds (3, 4, 7, 8, 9 and 11) display a similar cytotoxicity profile against the β-tubulin mutants compared to epothilone A (1) (see Table 1). In other words these compounds lose some activity against the clones PTX10 (β270) and A8 (β274) suggesting that residues 270 and 274 are important for the binding of these analogs to tubulin. However, the most active analog (11) still retains $IC_{50}$<10 nM for all of these cell lines. Furthermore, we found in the current study, and in agreement with previous reports (Nicolaou, K. C.; et al. *ChemBioChem* 2001, 1, 69-75; Giannakakou, P.; et al. *J. Biol. Chem.* 1997, 272, 17118-17125; Giannakakou, P.; et al. *Proc. Natl. Acad. Sci. USA* 2000, 97, 2904-2909) that the paclitaxel-selected clone PTX22 (β364) retains sensitivity to the epothilones, especially in the case of the most active analogs (9 and 11) where the relative resistance (RR) values are <1.

The cytotoxicity analysis was supplemented with data from two independent in vitro tubulin polymerization assays. In one assay, the fraction of tubulin polymerized into microtubules upon exposure to a given concentration of the respective compound was determined (see Table 2). In the other assay, tubulin polymerization kinetics upon exposure to the respective compounds was determined using purified rat brain tubulin through measurement of the absorbance at 350 nm (see FIG. 3). For this analysis, paclitaxel, epothilone A (1) and epothilone B (2) were used as controls while compounds 9, 11 and 12 were selected for in vitro analysis. Compound 12 had no in vitro activity consistent with the lack of cytotoxic activity for this compound (Table 1). Compounds 9 and 11 exhibited good in vitro activity although the maximum degree of tubulin polymerization induced by these compounds was smaller compared with that induced by epothilone A (1). However, the increased cytotoxic activity of compounds 9 and 11 relative to epothilone A (1) could potentially be explained by the faster kinetics of polymerization induced by compounds 9 and 11 [time to $A_{350}$=0.25 is <1 min for compounds 9 and 11, and 2 min for epothilone A (1)].

Figure 4:
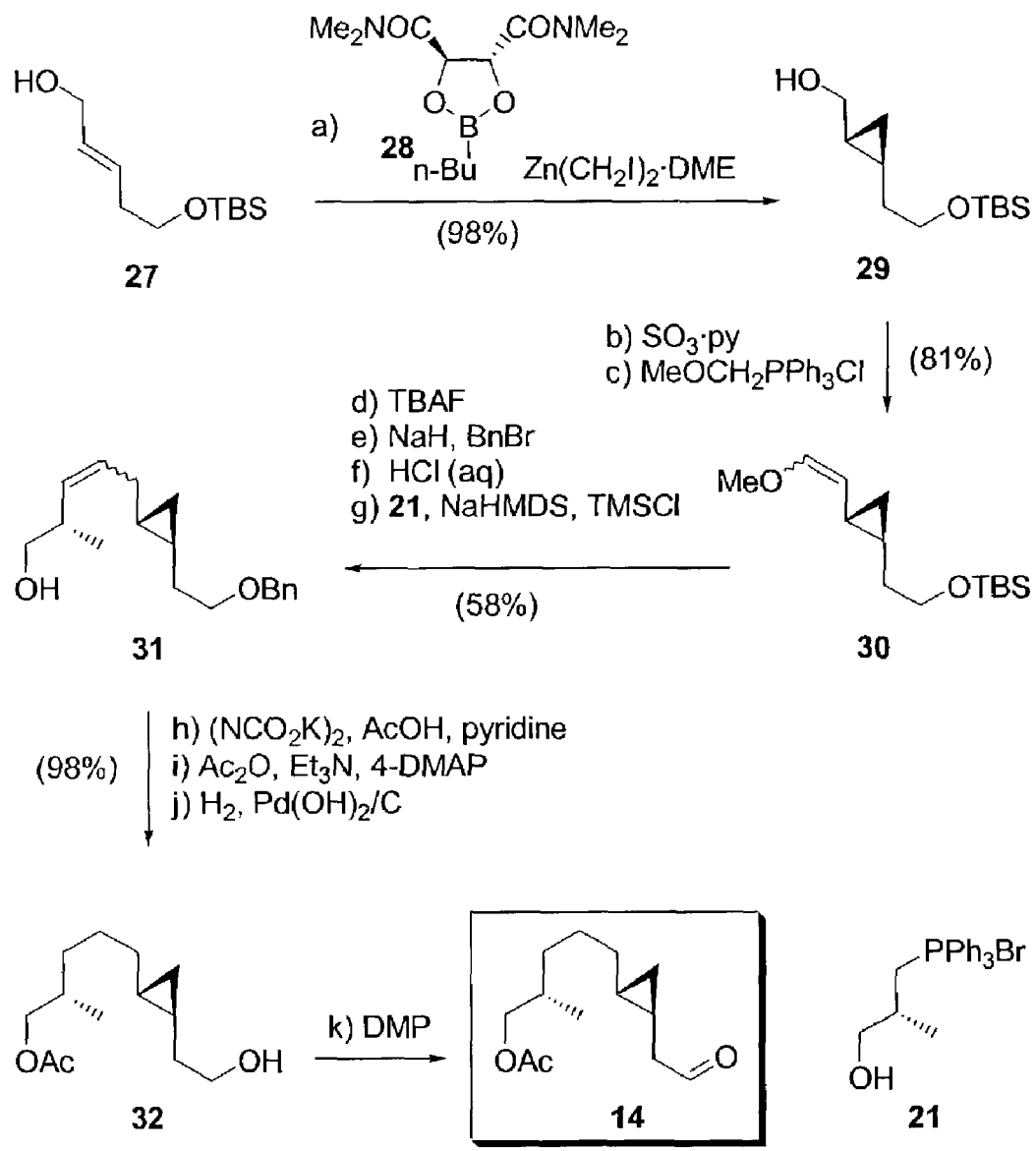
FIG. 4 illustrates a scheme showing the synthesis of aldehyde 14.

Finally, tubulin polymerization products of these compounds were examined by electron microscopy (FIG. 4) to rule out the potential increase in absorbance due to the formation of non-microtubule polymers. As seen in FIG. 4, all compounds tested induced the formation of microtubule polymers with the exception of compound 12 where no microtubules were observed.

DETAILED DESCRIPTION OF FIGURES

FIG. 1 shows the structures of a series of cyclopropyl and cyclobutyl epothilone analogs (3-12). Biological studies with the synthesized compounds led to the identification of epothilone analogs 3, 4, 7, 8, 9 and 11 as potent tubulin polymerization promoters and cytotoxic agents with (12R, 13S, 15S)-cyclopropyl 5-methylpyridine epothilone A (11) as the most powerful compound whose potencies (e.g. $IC_{50}$=0.6 nM against the 1A9 ovarian carcinoma cell line) approach those of epothilone B. These investigations led to a number of important structure-activity relationships, including the conclusion that neither the epoxide nor the stereochemistry at C12 are essential, while the stereochemistry at both C13 and C15 are crucial for biological activity. These studies also confirmed the importance of both the cyclopropyl and 5-methylpyridine moieties in conferring potent and potentially clinically useful biological properties to the epothilone scaffold.

FIG. 2 illustrates the retrosynthetic analysis used for the chemical synthesis of the designed 12,13-cycloalkane thiazole epothilone analogs 3-8. Nozaki-Hiyama-Kishi coupling (Takai, K.; et al. *Tetrahedron Lett.* 1983, 24, 5281-5284; Jin, H.; et al. *J. Am. Chem. Soc.* 1986, 108, 5644-5646), an aldol reaction and a Yamaguchi lactonization (Inanaga, J.; et al. *Bull. Chem. Soc. Jpn.* 1979, 52, 1989-1993; Mulzer, J.; et al. *Synthesis* 1992, 215-228; Nicolaou, K. C.; et al. *Chem. Eur. J.* 2000, 6, 2783-2800; Nicolaou, K. C.; et al. *J. Am. Chem. Soc.* 1997, 119, 7974-7991) were employed to disconnect the three strategic bonds as indicated, revealing building blocks 13-16, 17 and 18. The assembly and elaboration of these building blocks to the final targets was to follow the order shown in Scheme 1. Thus, coupling of the C7-C15 aldehyde fragment with the heterocyclic vinyl iodide, followed by elaboration and aldol reaction with the C1-C6 ketone segment would lead, upon further elaboration, to the desired seco-hydroxy acid. Cyclization according to the previous Yamaguchi strategy (Inanaga, J.; et al. *Bull. Chem. Soc. Jpn.* 1979, 52, 1989-1993; Mulzer, J.; et al. *Synthesis* 1992, 215-228; Nicolaou, K. C.; et al. *Chem. Eur. J.* 2000, 6, 2783-2800; Nicolaou, K. C.; et al. *J. Am. Chem. Soc.* 1997, 119, 7974-7991) would then furnish, upon deprotection, the desired epothilone analogs.

Figure 3:
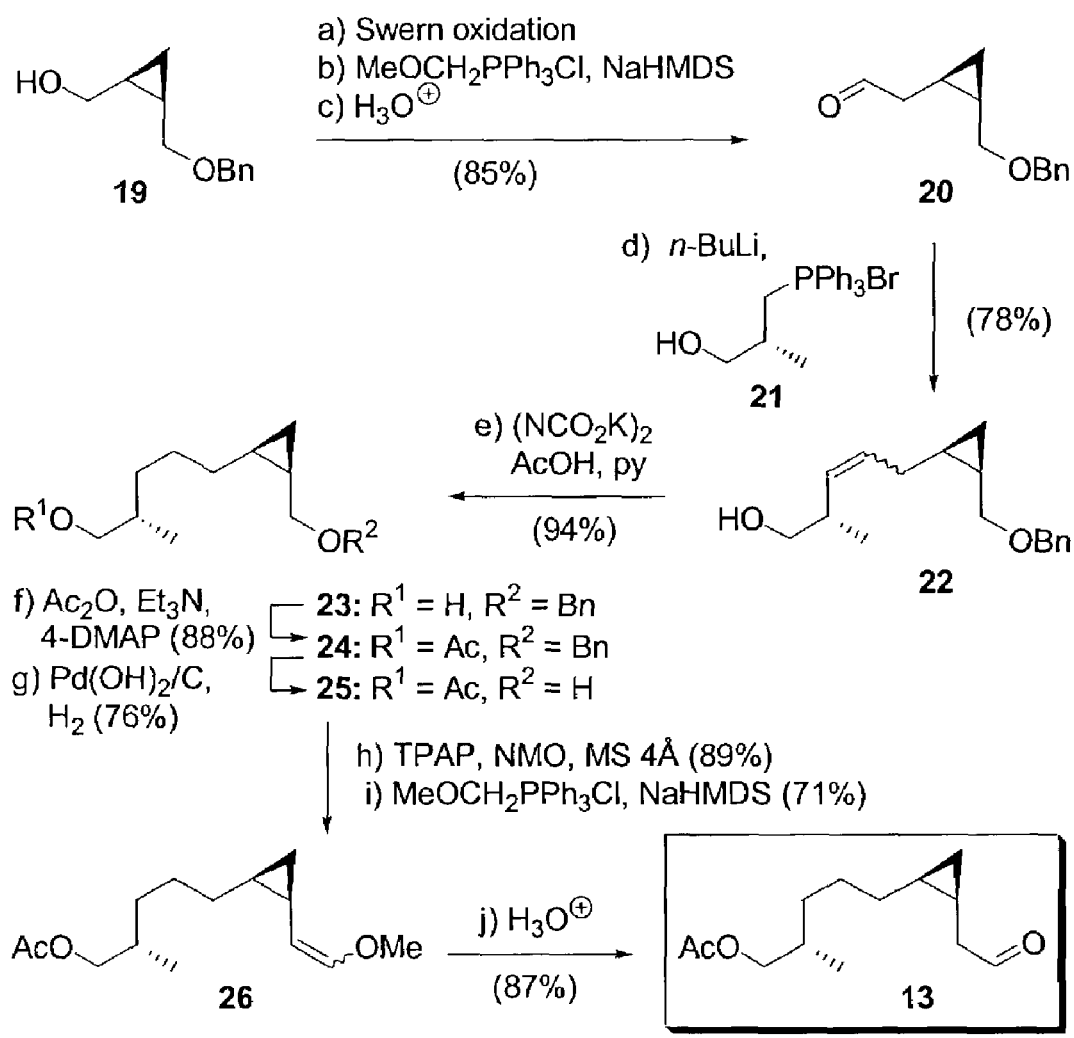
FIG. 3 illustrates a scheme showing the preparation of building block 13.

FIG. 3 is a scheme showing the preparation of building block 13. Reagents and Conditions: (a) $(COCl)_2$ (1.5 equiv), DMSO (2.0 equiv), $Et_3N$ (5.0 equiv), $CH_2Cl_2$, −78° C.; (b) $MeOCH_2PPh_3Cl$ (1.5 equiv), NaHMDS (1.4 equiv), THF, −78° C.; (c) cat. HCl, acetone:water 9:1, 65° C., 1 h, 85% over 3 steps; (d) 21 (1.5 equiv), n-BuLi (3.0 equiv), THF, −78° C., 78% (e) $(NCO_2K)_2$ (20 equiv), HOAc (40 equiv), MeOH, py, 25° C., 48 h, 94%; (f) $Ac_2O$ (1.1 equiv), $Et_3N$ (1.2 equiv), 4-DMAP (0.1 equiv), $CH_2Cl_2$, 25° C., 0.5 h, 88%; (g) 20% $Pd(OH)_2$/C, $H_2$ (1 atm), EtOAc:EtOH 1:1, 25° C., 2 h, 76%; (h) TPAP (0.05 equiv), NMO (1.5 equiv), MS 4 Å, CH$_2$Cl$_2$, 25° C., 1 h, 89%; (i) MeOCH$_2$PPh$_3$Cl (1.2 equiv), NaHMDS (1.1 equiv), THF, 0° C., 71%; (j) cat. HCl, acetone:water 9:1, 55-60° C., 2 h, 87%. 4-DMAP=4-dimethyl-aminopyridine, NaHMDS=sodium hexamethyldisilazide, NMO=N-methylmorpholine N-oxide, py=pyridine, TPAP=tetra-n-propyl ammonium perruthenate.

FIG. 4 is a scheme showing the synthesis of aldehyde 14. Reagents and Conditions: (a) DME (2.2 equiv), Et$_2$Zn (2.2 equiv), CH$_2$I$_2$ (4.4 equiv), 28 (1.2 equiv), CH$_2$Cl$_2$, 98% yield, >90% ee; (b) Et$_3$N (6.0 equiv), SO$_3$.py (3.0 equiv), CH$_2$Cl$_2$:DMSO 4:1, 0° C., 2 h; (c) MeOCH$_2$PPh$_3$Cl (1.5 equiv), NaHMDS (1.3 equiv), THF, −40 to 25° C., 12 h, 81% over 2 steps; (d) TBAF (1.5 equiv), THF, 25° C., 2 h; (e) NaH (1.5 equiv), BnBr (2.0 equiv), THF:DMF 5:1, 0 to 25° C., 10 h; (f) cat. HCl, acetone:water 9:1, 50° C., 5 h; (g) 21 (1.5 equiv), NaHMDS (2.8 equiv), TMSCl (1.5 equiv), THF, 58% over 4 steps; (h) (NCO$_2$K)$_2$ (20 equiv), HOAc (40 equiv), MeOH, py, 25° C., 7 h; (i) Ac$_2$O (2.0 equiv), Et$_3$N (5.0 equiv), 4-DMAP (0.1 equiv), CH$_2$Cl$_2$, 0° C., 20 min; (j) 20% Pd(OH)$_2$/C, H$_2$ (1 atm), EtOAc:EtOH 1:1, 25° C., 6 h, 98% over 3 steps; (k) DMP (1.2 equiv), CH$_2$Cl$_2$, 0 to 25° C., 40 min. 4-DMAP=4-dimethylaminopyridine, DMP=Dess-Martin periodinane, NaHMDS=sodium hexamethyldisilazide, py=pyridine.

Figure 5:
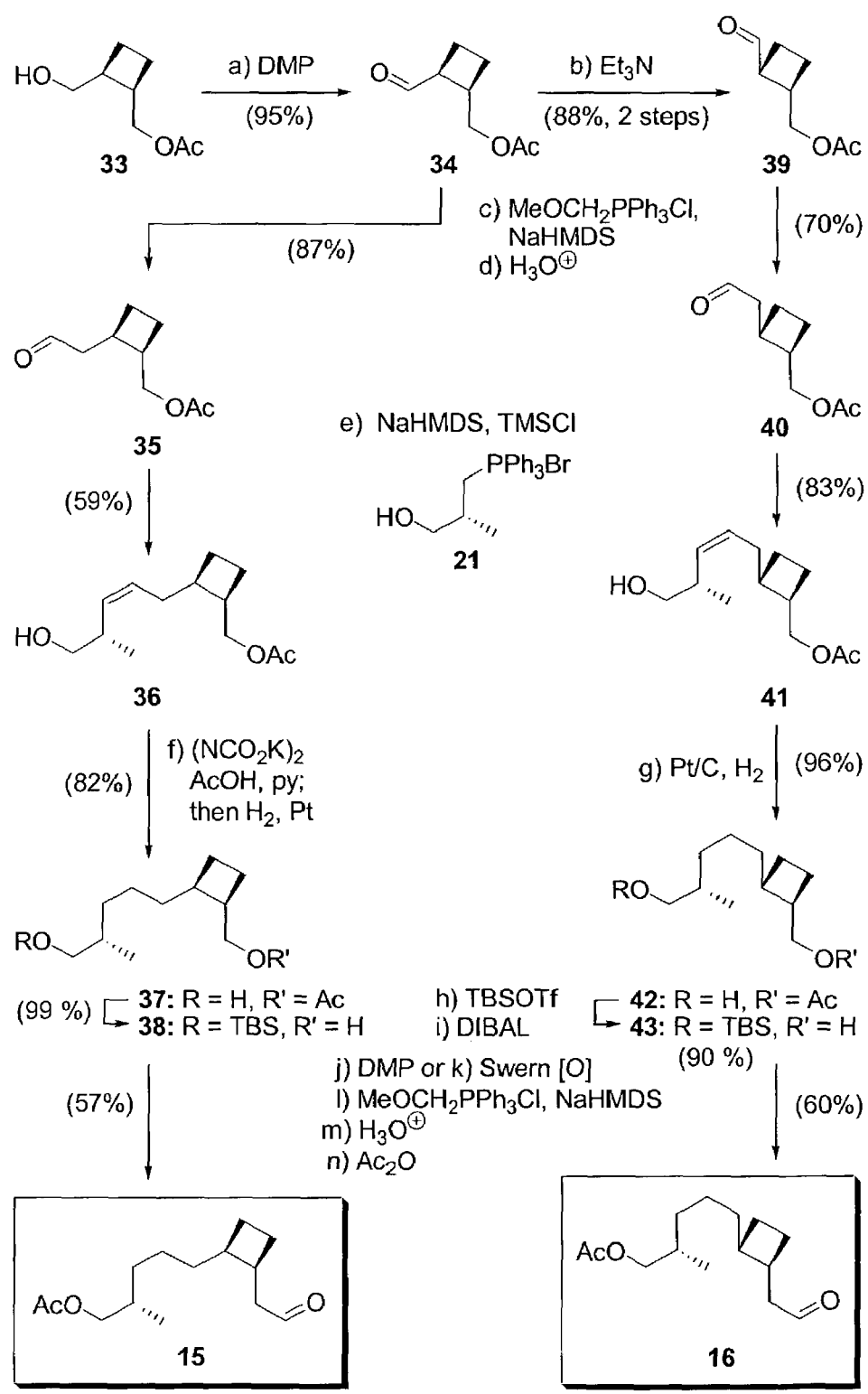
FIG. 5 illustrates a scheme for the synthesis building block aldehydes 15 and 16.

FIG. 5 is a scheme for the synthesis of building block aldehydes 15 and 16. Reagents and Conditions: (a) DMP (1.2 equiv), NaHCO$_3$ (5.0 equiv), CH$_2$Cl$_2$, 25° C., 3 h, 95%; (b) starting with alcohol 33: (COCl)$_2$ (1.1 equiv), DMSO (2.2 equiv), Et$_3$N (5.0 equiv), CH$_2$Cl$_2$, −78° C.; then Et$_3$N, 25° C., 5 days, 88% over 2 steps; c) MeOCH$_2$PPh$_3$Cl (1.15 equiv), NaHMDS (1.10 equiv), THF, −78 to 25° C., 89%; (d) 0.12 N HCl (aq):acetone (1:9), reflux, 1 h, 98% (35), 94% (40); (e) 21 (2.0 equiv), NaHMDS (3.8 equiv), THF, 0° C., 2 h; then TMSCl (2.0 equiv), 25° C., 20 min; then 35 (or 40), THF, −78 to 25° C., 20 h, 59% (36), 83% (41); (f) (NCO$_2$K)$_2$ (20 equiv), AcOH (40 equiv), py:MeOH (5:1), 25° C., 48 h; then PtO$_2$ (0.05 equiv), H$_2$ (1 atm), MeOH, 25° C., 20 min, 82%; (g) 10 wt % Pt on carbon (0.02 equiv), EtOAc, 25° C., 8 h, 96%; (h) TBSOTf (1.0 equiv), 2,6-lutidine (2.5 equiv), CH$_2$Cl$_2$, −78 to 0° C., 20 min; (i) DIBAL (2.0 equiv), CH$_2$Cl$_2$, −78° C., 5 min, 99% (38), 90% (43) for 2 steps; (j) DMP (1.2 equiv), NaHCO$_3$ (5.1 equiv), CH$_2$Cl$_2$, 25° C., 3 h, 94%; (k) (COCl)$_2$ (1.1 equiv), DMSO (2.2 equiv), Et$_3$N (5.0 equiv), CH$_2$Cl$_2$, −78 to 25° C., 97%; (l) MeOCH$_2$PPh$_3$Cl (1.15 equiv), NaHMDS (1.10 equiv), THF, −78 to 25° C.; (m) 0.12 N HCl (aq):acetone (1:9), reflux, 1 h; (n) Ac$_2$O (1.1 equiv), Et$_3$N (2.5 equiv), 4-DMAP (0.02 equiv), CH$_2$Cl$_2$, 0° C., 20 min, 60% (15), 62% (16) for 3 steps. DIBAL=diisobutylaluminum hydride, 4-DMAP=4-dimethylamino-pyridine, DMP=Dess-Martin periodinane, NaHMDS=sodium hexamethyldisilazide, py=pyridine, TMSCl=chlorotrimethylsilane.

Figure 6:
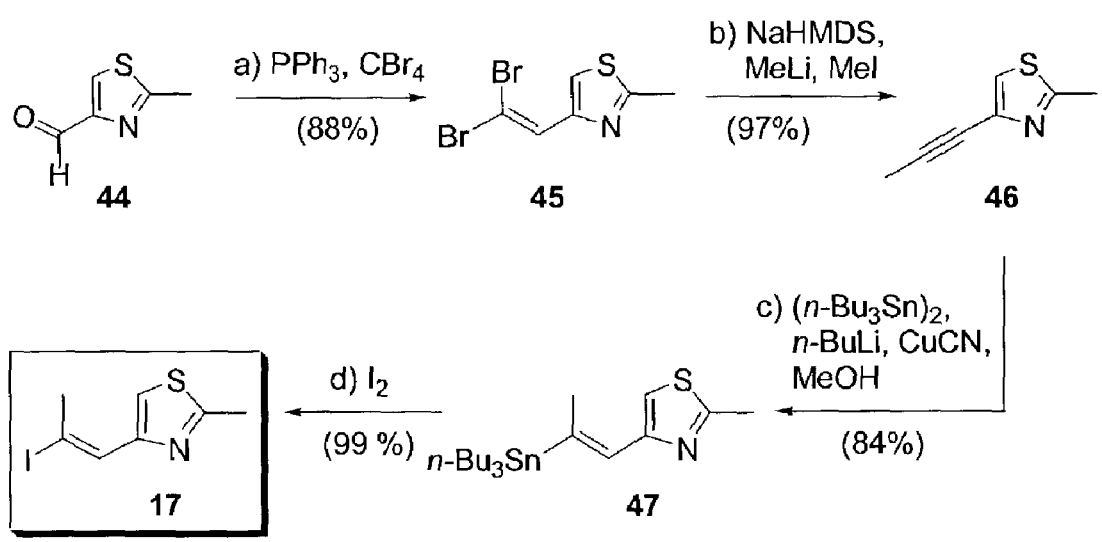
FIG. 6 illustrates a scheme that illustrates the synthesis of thiazole vinyl iodide 17.

FIG. 6 is a scheme that illustrates the synthesis of thiazole vinyl iodide 17. Reagents and Conditions: (a) PPh$_3$ (4.0 equiv), CBr$_4$ (2.0 equiv), CH$_2$Cl$_2$, 0° C., 4 h, 88%; (b) NaHMDS (1.0 equiv), MeLi (2.0 equiv), MeI (5.0 equiv), −78 to 25° C., 12 h, 97%; (c) n-BuLi (4.0 equiv), (n-Bu$_3$Sn)$_2$ (4.0 equiv), CuCN (2.0 equiv), MeOH (110 equiv), THF, 87%; (d) I$_2$ (1.1 equiv), CH$_2$Cl$_2$, 0° C., 99%. NaHMDS=sodium hexamethyidisilazide.

Figure 7:
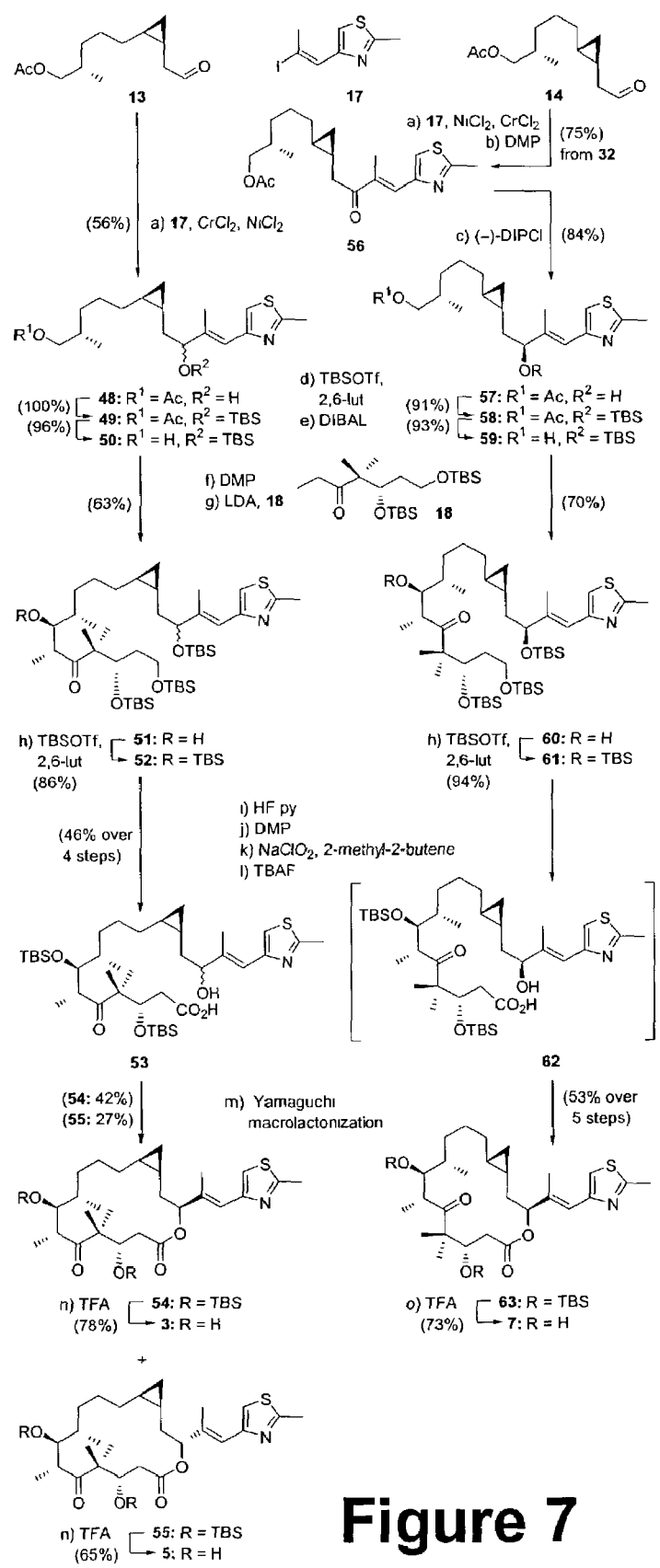
FIG. 7 illustrates a scheme showing the synthesis of epothilone analogs 3, 5 and 7.

FIG. 7 is a scheme showing the synthesis of epothilone analogs 3, 5, and 7. Reagents and Conditions: (a) 17 (1.5-2.0 equiv), CrCl$_2$ (10-13 equiv), NiCl$_2$ (0.02-0.13 equiv), DMSO, 25° C., 6-12 h, 56% (48), 91% from 32; (b) DMP (1.2 equiv), CH$_2$Cl$_2$, 0 to 25° C., 0.5 h, 83%; (c) (−)-DIPCI (3.0 equiv), Et$_2$O, −15 to 25° C., 18 h, 84%; (d) TBSOTf (1.1-2.0 equiv), 2,6-lutidine (2.5 equiv), CH$_2$Cl$_2$, −78° C., 0.5-1 h, 91-100%; (e) DIBAL (2.0-3.1 equiv), CH$_2$Cl$_2$, −78° C., 15 min-1 h, 93-96%; (f) DMP (1.2 equiv), CH$_2$Cl$_2$, 25° C., 1.5 h; (g) LDA (3.1 equiv), 18 (3.0 equiv), THF, −78° C., 4 min, 63% (51), 70% (60); (h) TBSOTf (2.0 equiv), 2,6-lutidine (2.5 equiv), CH$_2$Cl$_2$, −20 to 25° C., 1.5-12 h, 86% (52), 94% (61); (i) HF.py, py, 0-25° C., 3-4 h; (j) DMP (1.2-1.5 equiv), NaHCO$_3$ (1.5 equiv), CH$_2$Cl$_2$, 25° C., 15 min-2 h; (k) NaClO$_2$ (5.0 equiv), 2-methyl-2-butene (7.5 equiv), NaH$_2$PO$_4$ (2.5 equiv), t-BuOH:H$_2$O 4:1, 25° C., 10-20 min; (l) TBAF (12 equiv), THF, 25° C., 16-26 h, 46% over 4 steps (53); (m) 2,4,6-trichlorobenzoylchloride (2.4 equiv), Et$_3$N (6.0 equiv), THF, 0° C., 1 h, then 4-DMAP (2.2 equiv), toluene, 75° C., 3-11 h, 42% (54), 27% (55), 53% over 5 steps (63); (i) 20% TFA in CH$_2$Cl$_2$, 0° C., 2 h, 78% (3), 65% (5); (o) 25% TFA in CH$_2$Cl$_2$, 25° C., 7 h, 73% DIBAL=diisobutylaluminum hydride, DIPCI=diisopinocampheyl chloroborane, 4-DMAP=4-dimethyl-aminopyridine, DMP=Dess-Martin periodinane, LDA=lithium diisopropylamide, NaHMDS=sodium hexamethyidisilazide, py=pyridine, TBAF=tetrabutylammonium fluoride.

Figure 8:
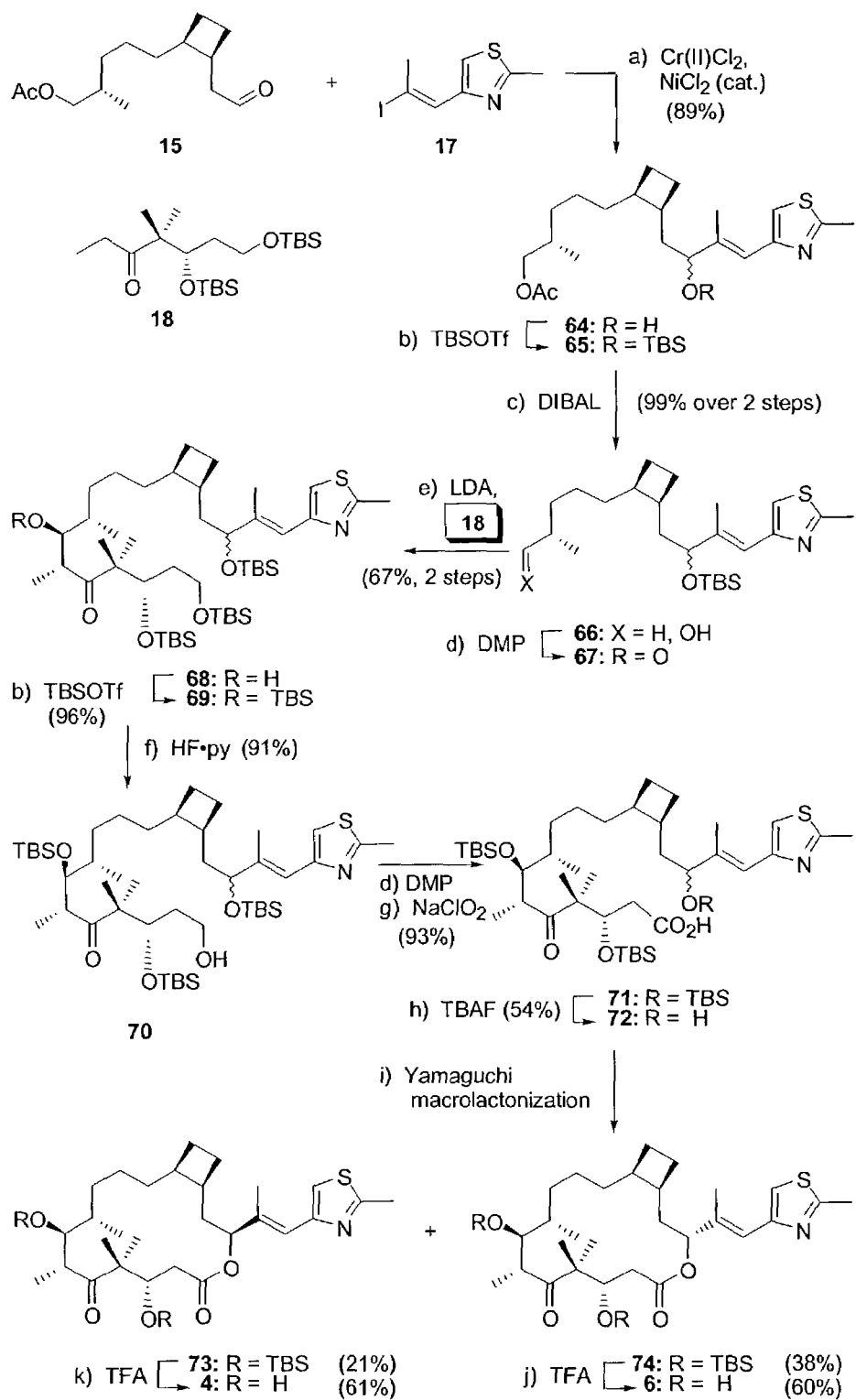
FIG. 8 illustrates a scheme for the synthesis of cis-cyclobutyl epothilone analogs 4 and 6.

FIG. 8 is a scheme which shows the synthesis of cis-cyclobutyl epothilone analogs 4 and 6. Reagents and Conditions: (a) 17 (1.5 equiv), CrCl$_2$ (12.6 equiv), NiCl$_2$ (0.13 equiv), DMSO, 25° C., 6 h, (89%, 2:3 mixture of C15 epimers); (b) TBSOTf (1.0 equiv), 2,6-lutidine (2.5 equiv), CH$_2$Cl$_2$, −78 to 0° C., 20 min; (c) DIBAL (2.0 equiv), CH$_2$Cl$_2$, −78° C., 5 min, 99% for 2 steps; (d) DMP (1.2 equiv), CH$_2$Cl$_2$, 25° C., 1.5 h; (e) LDA (3.1 equiv), 18 (3.0 equiv), THF, −78° C., 4 min, 67% for 2 steps; (f) TBSOTf (2.0 equiv), 2,6-lutidine (2.5 equiv), CH$_2$Cl$_2$, −20 to 25° C., 1.5 or 12 h, 96%; (g) HF.py, py, THF, 0 to 25° C., 3 h, 91%; (h) DMP (1.2-1.5 equiv), NaHCO$_3$ (1.5 equiv), CH$_2$Cl$_2$, 25° C., 15 min or 2 h; (i) NaClO$_2$ (5.0 equiv), 2-methyl-2-butene (7.5 equiv), NaH$_2$PO$_4$ (2.5 equiv), t-BuOH:H$_2$O 4:1, 25° C., 10-20 min, 93% for 2 steps; (j) TBAF (12 equiv), THF, 25° C., 16-26 h, 54%; (k) 2,4,6-trichloro-benzoylchloride (2.4 equiv), Et$_3$N (6.0 equiv), THF, 0° C., 1 h, then 4-DMAP (2.2 equiv), toluene, 75° C., 3 or 11 h, 21% (73), 38% (74); (l) 20 v/v % TFA in CH$_2$Cl$_2$, 25° C., 1 or 8 h, 61% (4), 60% (6). 4-DMAP=4-dimethylamino-pyridine, DMP=Dess-Martin periodinane, LDA=lithium diisopropylamide, py=pyridine, TBAF=tetrabutylammonium fluoride.

FIG. 9 is a scheme showing the synthesis of the trans-cyclobutyl epothilone analog 8. Reagents and Conditions: (a) 17 (1.5 equiv), CrCl$_2$ (12.6 equiv), NiCl$_2$ (0.13 equiv), DMSO, 25° C., 6 h, 91%; (b) DMP (1.2 equiv), NaHCO$_3$ (5.0 equiv), CH$_2$Cl$_2$, 25° C., 3 h; (c) (−)-DIPCI (3.0 equiv), Et$_2$O, −15 to 25° C., 18 h, 47% for 2 steps; (d) TBSOTf (1.0 equiv), 2,6-lutidine (2.5 equiv), CH$_2$Cl$_2$, −78 to 0° C., 20 min; (e) DIBAL (2.0 equiv), CH$_2$Cl$_2$, 78° C., 5 min, 84% for 2 steps; (f) DMP (1.2 equiv), CH$_2$Cl$_2$, 25° C., 1.5 h; (g) LDA (3.1 equiv), 18 (3.0 equiv), THF, −78° C., 4 min, 75% for 2 steps; (h) TBSOTf (2.0 equiv), 2,6-lutidine (2.5 equiv), CH$_2$Cl$_2$, −20 to 25° C., 1.5 or 12 h, 96%; (i) HF.py, py, THF, 0 to 25° C., 3 h, 81%; (j) DMP (1.2-1.5 equiv), NaHCO$_3$ (1.5 equiv), CH$_2$Cl$_2$, 25° C., 15 min or 2 h; (k) NaClO$_2$ (5.0 equiv), 2-methyl-2-butene (7.5 equiv), NaH$_2$PO$_4$ (2.5 equiv), t-BuOH:H$_2$O 4:1, 25° C., 10-20 min; (l) TBAF (12 equiv), THF, 25° C., 16-26 h, 47% for 3 steps; (m) 2,4,6-trichloro-benzoylchloride (2.4 equiv), Et$_3$N (6.0 equiv), THF, 0° C., 1 h; then 4-DMAP (2.2 equiv), toluene, 75° C. 3-11 h, 50%; (n) 20% TFA in CH$_2$Cl$_2$, 0° C., 2 h, 79%. DIBAL=diisobutyl-aluminum hydride, DIPCI=diisopinocampheyl-chloroborane, 4-DMAP=4-dimethylamino-pyridine, DMP=Dess-Martin periodinane, LDA=lithium diisopropylamide, py=pyridine, TBAF=tetrabutylammonium fluoride.

Figure 10:
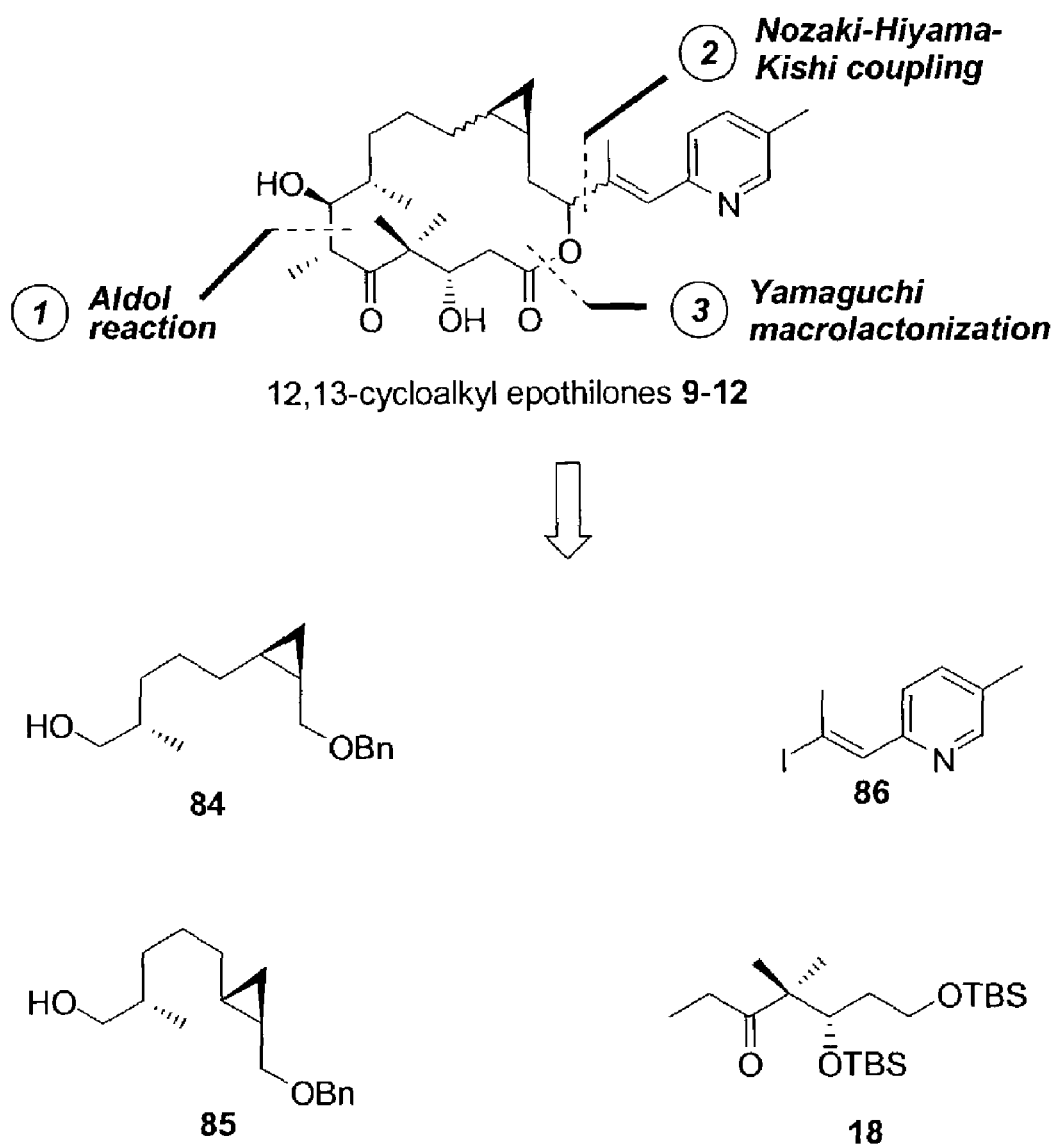
FIG. 10 illustrates the retrosynthetic analysis and key fragments for epothilone analogs 9-12.

FIG. 10 shows the retrosynthetic analysis and key fragments for epothilone analogs 9-12. The strategy devised for the construction of the pyridine cycloalkane epothilones (9-12) is similar to that utilized for the total synthesis of their thiazole counterparts except for the reversal of the coupling order of the fragments. Thus, the aldol reaction of building blocks 84 and 85 with ketone 18 will now precede the Nozaki-Hiyama-Kishi coupling with vinyl iodide 86.

Figure 11:
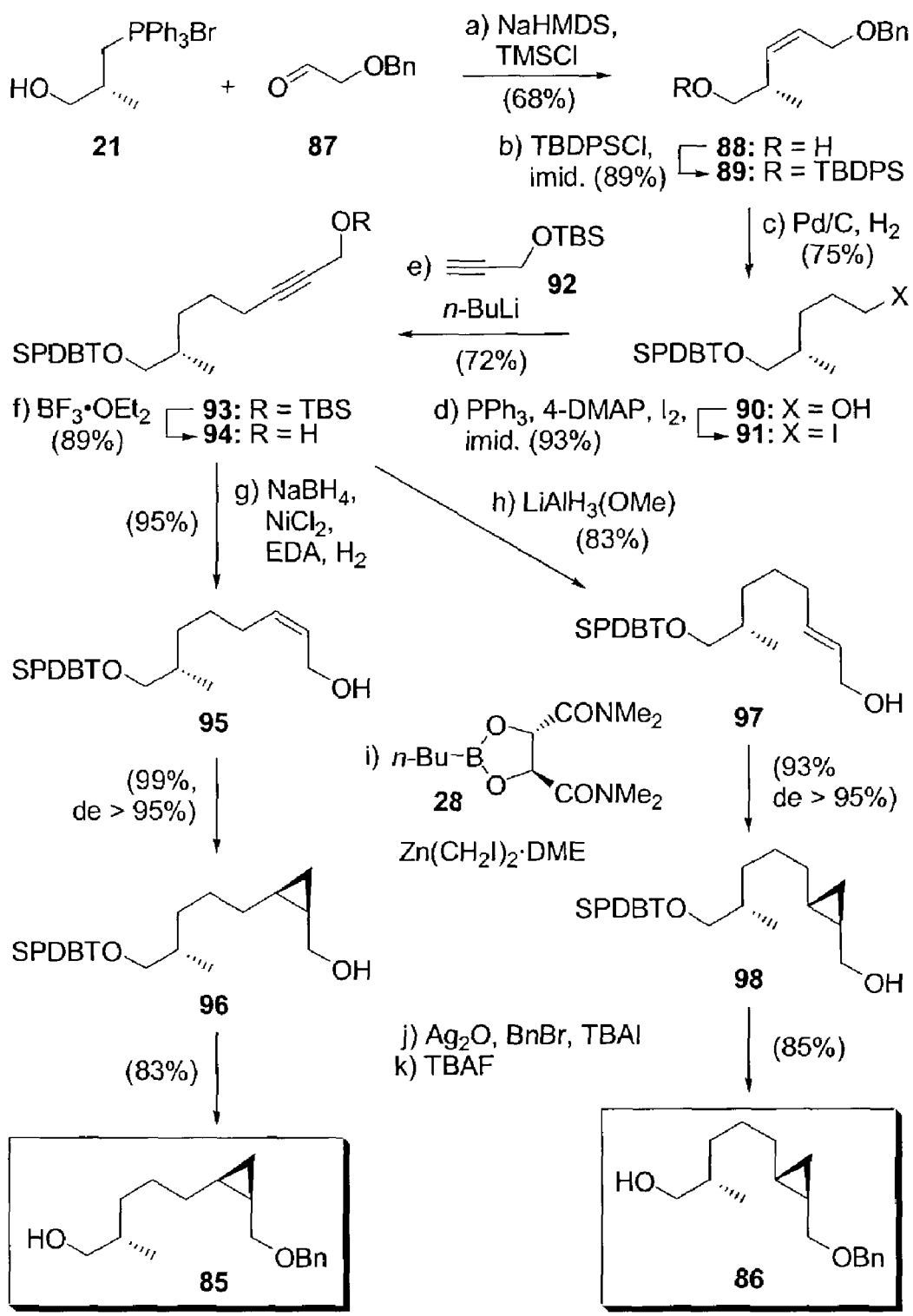
FIG. 11 illustrates a scheme for the synthesis of alcohols 85 and 86.

FIG. 11 is a scheme for the synthesis of alcohols 85 and 86. Reagents and Conditions: (a) NaHMDS (2.1 equiv), TMSCI (1.1 equiv), THF, −78 to 25° C., 6 h, 68%; (b) TBDPSCI (1.1 equiv), imidazole (2.0 equiv), DMF, 25° C., 1 h, 89%; (c) 10% Pd/C, H$_2$ (1 atm), MeOH:THF 5:1, 50° C., 10 h, 75%; (d) PPh$_3$ (1.4 equiv), 4-DMAP (0.01 equiv), I$_2$ (1.5 equiv), imidazole (2.0 equiv), MeCN/Et$_2$O, 25° C., 1 h, 93%; (e) n-BuLi (3.3 equiv), 3-(tert-butyldimethylsilyloxy)propyne (3.5 equiv), THF/HMPA, −78 to −30° C., 2.5 h, 72%; (f) BF$_3$.OEt$_2$ (2.0 equiv), CH$_2$Cl$_2$, 25° C., 1.5 h, 89%; (g) NiCl$_2$ (1.0 equiv), NaBH$_4$ (1.0 equiv), EDA (3.0 equiv), H$_2$ (1 atm), EtOH, 0° C., 1 h, 95%; (h) LiAlH$_4$ (1.0 equiv), MeOH (1.0 equiv), THF, 50° C., 0.5 h, 83%; (i) DME (2.2 equiv), Et$_2$Zn (2.2 equiv), CH$_2$I$_2$ (4.4 equiv), 28 (1.2 equiv), CH$_2$Cl$_2$, −15 to 25° C., 6 h, 99% (96), 93% (98); (j) Ag$_2$O (3.0 equiv), BnBr (2.6 equiv), TBAI (0.1 equiv), toluene, 24 h, 25 to 50° C.; (k) TBAF (5.0 equiv), THF, 25° C., 4 h, 83% (85), 85% (86) over 2 steps. 4-DMAP=4-dimethylaminopyridine, DME=dimethoxyethane, DMP=Dess-Martin periodinane, EDA=ethylenediamine, HMPA=hexamethyl-phosphoramide, NaHMDS=sodium hexamethyldisilazide, TBAF=tetrabutylammonium fluoride, TBAI=tetrabutylammonium iodide.

Figure 12:
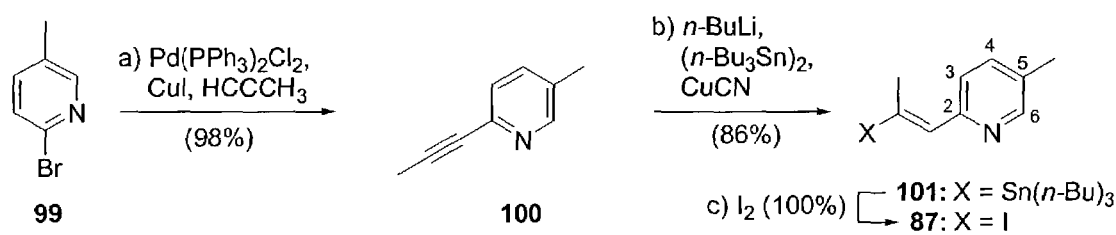
FIG. 12 illustrates the synthesis of pyridine iodide 87.

FIG. 12 shows the synthesis of the pyridine vinyl alcohol 87. A Sonogashira coupling of 5-methyl-2-bromopyridine 99 with propyne (Arcadi, A.; et al. *Tetrahedron* 1994, 50, 437-452) yielded alkyne 100 in 98% yield. This was then hydrostannylated, and the tin was exchanged for iodine (86% for two steps) by the same method as that employed to prepare the thiazole side chain precursor 17 (Scheme 5), thus yielding iodide 87 via stannane 101 (100% yield). Reagents and Conditions: (a) Pd(PPh$_3$)$_2$Cl$_2$ (0.01 equiv), CuI (0.02 equiv), propyne (1 atm), DMF/(i-Pr)$_2$NH, 25° C., 3 h, 98%; (b) n-BuLi (4.0 equiv), (n-Bu$_3$Sn)$_2$ (4.0 equiv), CuCN (2.0 equiv), MeOH (110 equiv), THF, −10° C., 15 h, 86%; (c) I$_2$ (1.05 equiv), CH$_2$Cl$_2$, 25° C., 5 min, 100%.

Figure 13:
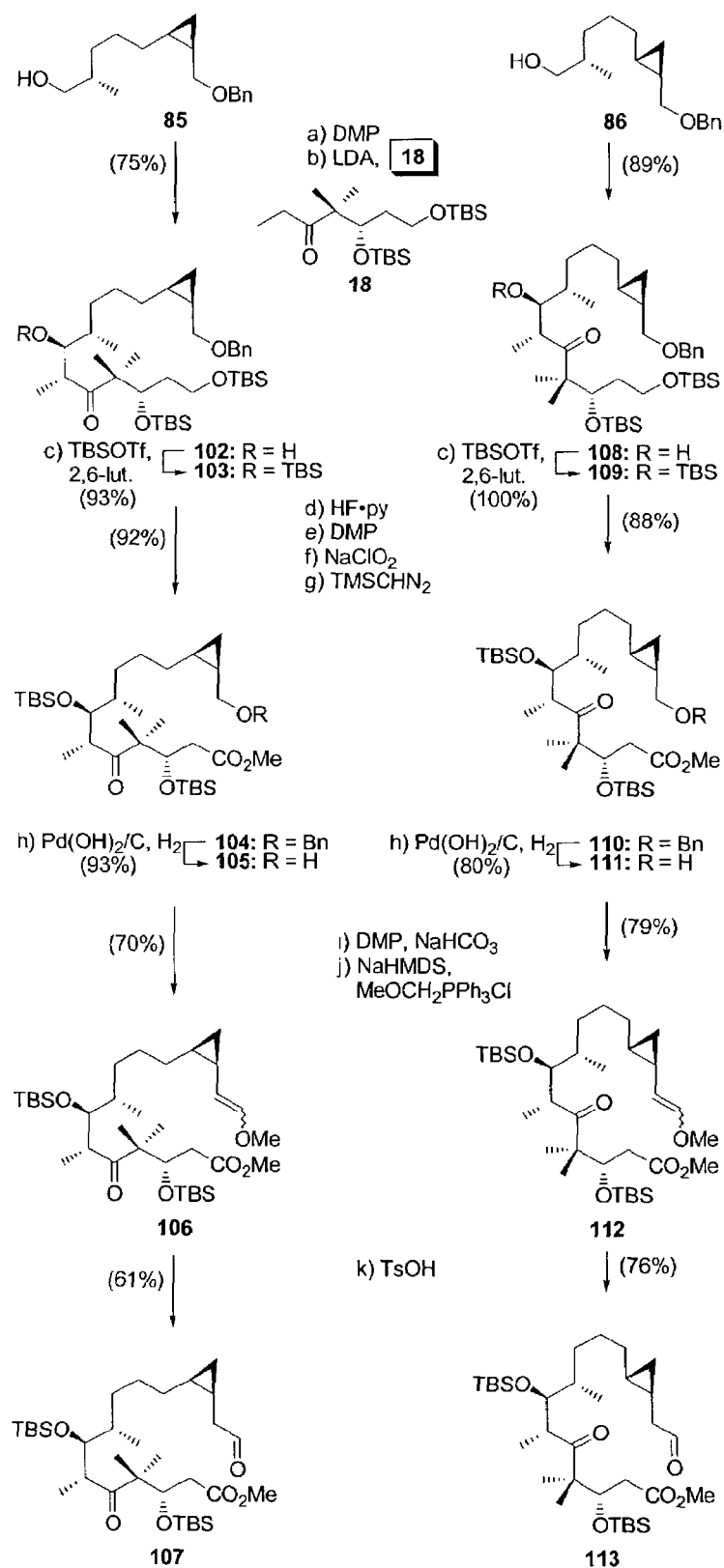
FIG. 13 illustrates a scheme for the synthesis of precursor aldehydes 107 and 113.

FIG. 13 is a scheme showing the synthesis of aldehydes 107 and 113. Reagents and Conditions: (a) DMP (1.2 equiv), CH$_2$Cl$_2$, 25° C., 1.5 h; (b) LDA (2.5 equiv), 18 (2.4 equiv), THF, −78° C., 4 min, 75% (102), 89% (108) over 2 steps, (c) TBDPSOTf (4.0 equiv), 2,6-lutidine (5.0 equiv), CH$_2$Cl$_2$, −20 to 25° C., 1 h, 93% (103), 100% (109); (d) HF.py, py, 25° C., 2 h; (e) DMP (1.2 equiv), NaHCO$_3$ (1.5 equiv), CH$_2$Cl$_2$, 25° C., 6 h; (f) NaClO$_2$ (5.0 equiv), 2-methyl-2-butene (7.5 equiv), NaH$_2$PO$_4$ (2.5 equiv), t-BuOH:H$_2$O 4:1, 25° C., 10 min; (g) TMSCHN$_2$ (2.0 equiv), MeOH:benzene 1:1, 92% (104), 88% (110) over 4 steps; (h) 20% Pd(OH)$_2$/C, H$_2$ (1 atm), EtOAc:EtOH 1:1, 25° C., 6 h, 93% (105), 80% (111); (i) DMP (1.2 equiv), NaHCO$_3$ (1.5 equiv), CH$_2$Cl$_2$, 25° C., 1.5 h; (j) MeOCH$_2$PPh$_3$Cl (1.5 equiv), NaHMDS (1.3 equiv), THF, −40 to 25° C., 70% (106), 79% (112); (k) TsOH (20 equiv), dioxane:H$_2$O 10:1, 50° C., 5 h; then silylation as in (c), 61% (107), 76% (113). DMP=Dess-Martin periodinane, NaHMDS=sodium hexamethyidisilazide, py=pyridine.

Figure 14:
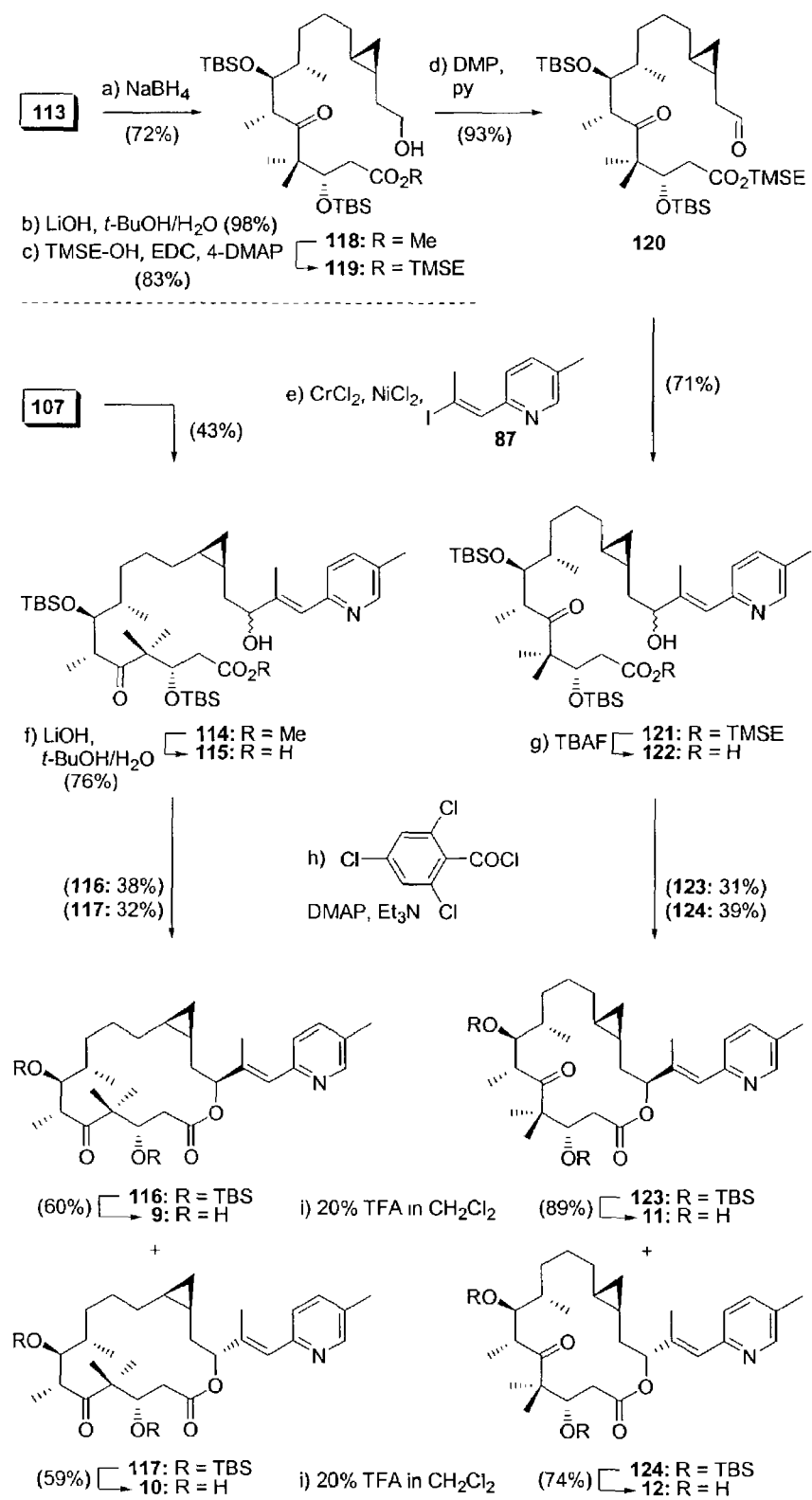
FIG. 14 illustrates the synthesis of cyclopropyl pyridine analogs of epothilone 9, 10, 11 and 12.

FIG. 14 shows the synthesis of cyclopropyl pyridine analogs of epothilone, 9, 10, 11, and 12. Reagents and Conditions: (a) NaBH$_4$ (1.1 equiv), CH$_2$Cl$_2$/EtOH, −78° C., 1 h, 72%; (b) LiOH, H$_2$O/t-BuOH, 40° C., 48 h, 98%; (c) EDC (2.0 equiv), 4-DMAP (0.5 equiv), TMSE-OH: CH$_2$Cl$_2$2:1, 25° C., 2 h, 83%; (d) DMP (2.5 equiv), py (10 equiv), CH$_2$Cl$_2$, 0° C., 2.5 h, 93%; (e) 87 (2.0 equiv), CrCl$_2$ (10 equiv), NiCl$_2$ (0.02 equiv), DMSO, 25° C., 12 or 36 h, 43% (114), 71% (121); (f) LiOH, H$_2$O:t-BuOH 2:3, 25° C., 4 days, 76%; (g) TBAF (18 equiv), THF, 0° C., 2 h; (h) 2,4,6-trichlorobenzoylchloride (9.0 equiv), Et$_3$N (22 equiv), THF, 0° C., 1 h, then 4-DMAP (3.0 equiv), toluene, 75° C., 3 h, 38% (116), 32% (117), 31% (123), 39% (124); (i) 20% TFA in CH$_2$Cl$_2$, 25° C., 2-22 h, 60% (9), 59% (10), 89% (11), 74% (12). 4-DMAP=4-dimethylaminopyridine, DMP=Dess-Martin periodinane, EDC=1-ethyl-3-(3-dimethylaminopropyl)carbodiimide hydrochloride, py=pyridine, TBAF=tetrabutylammonium fluoride, TMSE=2-(trimethylsilyl)ethyl.

FIG. 15 is a table that displays the cytotoxicity of epothilones 1 through 12 and paclitaxel against 1A9 human ovarian carcinoma cells and β-tubulin mutant cell lines selected with paclitaxel or epothilone A.[a] The antiproliferative effects of the tested compounds against the parental 1A9 and the paclitaxel- and epothilone-selected drug resistant clones (PTX10, PTX22 and A8, respectively) were assessed in a 72 h growth inhibition assay using the SRB (sulforhodamine-B) assay (Skehan, P.; et al. *J. Natl. Cancer Inst.* 1990, 82, 1107-1112). IC$_{50}$ values for each compound are given in nM and represent the mean of 3-5 independent experiments±standard error of the mean. Relative resistance (RR) is calculated as an IC$_{50}$ value for each resistant subline divided by that for the parental cell line (1A9).[b] Data from reference 3. CP=cyclopropyl, CB=cyclobutyl, na=not applicable, nd=not determined, py=5-methylpyridine side chain.

FIG. 16 is a table of tubulin polymerization potency[a] and cytotoxicity[b] of epothilones 1 through 12 and paclitaxel against human epidermoid cancer cell lines.[a]% TP=percent tubulin polymerized after incubation of tubulin with a known concentration of compound (typically 3 μM).[b] Cytotoxicity towards human cancer cell lines as IC$_{50}$ values given in nM. KB-31: epidermoid Taxol®-sensitive, KB-8511: epidermoid Taxol®-resistant (due to P-gp over expression).

What is claimed is:
1. A compound of formula I,

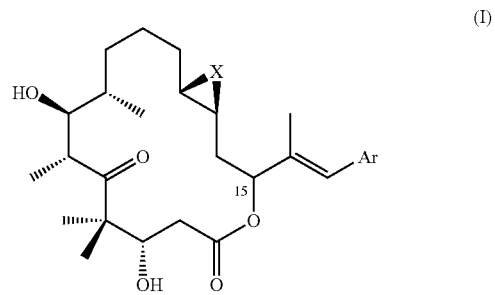

(I)

wherein

X is a diradical selected from the group consisting of —O—, —C(Y$^1$)(Y$^2$)—, and —C(Y$^1$)(Y$^2$)—C(Y$^1$)(Y$^2$)—, Y$^1$ and Y$^2$ are each radicals independently selected from the group consisting of —H, —F, —Cl and —Br; and Ar is a radical represented by the following structure:

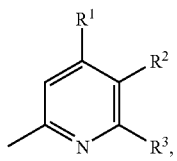

wherein
- R¹ either forms a first fused ring structure with R² or is a radical selected from —H and a C1-C6 branched or straight chain alkyl represented by —(C(Z¹)(Z²)(Z³))$_n$, where $1 \leq n \leq 6$ and Z¹, Z², and Z³ are each a radical independently selected from the group consisting of —H, —F, —Cl, —Br, —OH, —NH$_2$, and —(C(Z¹)(Z²)(Z³)), with a proviso that, if any one of Z¹, Z², or Z³ is —OH or —NH$_2$, then each of the remaining Z¹, Z², and Z³ is independently selected from the group consisting of —H and —(C(Z¹)(Z²)(Z³));
- R² either forms the first fused ring structure with R¹ or forms a second fused ring structure with R³ or is a radical selected from the group consisting of —H and a C1-C6 branched or straight chain alkyl represented by —(C(Z¹)(Z²)(Z³))$_n$, where $1 \leq n \leq 6$ and Z¹, Z², and Z³ are each a radical independently selected from the group consisting of —H, —F, —Cl, —Br, —OH, —NH$_2$, and —(C(Z¹)(Z²)(Z³)), with a proviso that, if any one of Z¹, Z², or Z³ is —OH or —NH$_2$, then each of the remaining Z¹, Z², and Z³ is independently selected from the group consisting of —H and —(C(Z¹)(Z²)(Z³));
- R³ either forms said second fused ring structure with R² is a radical selected from the group consisting of —H and a C1-C6 branched or straight chain alkyl represented by —(C(Z¹)(Z²)(Z³))$_n$, where $1 \leq n \leq 6$ and Z¹, Z², and Z³ are each a radical independently selected from the group consisting of —H, —F, —Cl, —Br, —OH, —NH$_2$, and —(C(Z¹)(Z²)(Z³)), with a proviso that, if any one of Z¹, Z², or Z³ is —OH or —NH$_2$, then each of the remaining Z¹, Z², and Z³ is independently selected from the group consisting of —H and —(C(Z¹)(Z²)(Z³));
- said first or second fused ring structure is either an aromatic or heteroaromatic 5- or 6-membered fused ring with or without C1-C6 branched or straight chain alkyl substituents; and
- the stereogenic center in 15-position can have R or S configuration, or a salt thereof.

2. A compound of formula I according to claim 1 wherein the stereogenic center in 15-position has S configuration, thus representing a compound of formula I-S, (I-S)

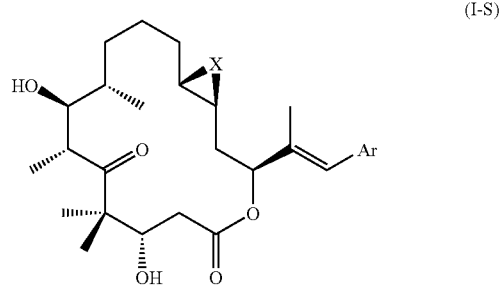

wherein
- X is a diradical selected from the group consisting of —O—, —C(Y¹)(Y²)—, and —C(Y¹)(Y²)—C(Y¹)(Y²)—,
- Y¹ and Y² are each radicals independently selected from the group consisting of —H, —F, —Cl and —Br; and
- Ar is a radical represented by the following structure:

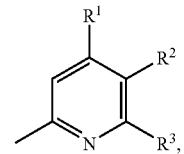

wherein
- R¹ either forms a first fused ring structure with R² or is a radical selected from —H and a C1-C6 branched or straight chain alkyl represented by —(C(Z¹)(Z²)(Z³))$_n$, where $1 \leq n \leq 6$ and Z¹, Z², and Z³ are each a radical independently selected from the group consisting of —H, —F, —Cl, —Br, —OH, —NH$_2$, and —(C(Z¹)(Z²)(Z³)), with a proviso that, if any one of Z¹, Z², or Z³ is —OH or —NH$_2$, then each of the remaining Z¹, Z², and Z³ is independently selected from the group consisting of —H and —(C(Z¹)(Z²)(Z³));
- R² either forms the first fused ring structure with R¹ or forms a second fused ring structure with R³ is a radical selected from the group consisting of —H and a C1-C6 branched or straight chain alkyl represented by —(C(Z¹)(Z²)(Z³))$_n$, where $1 \leq n \leq 6$ and Z¹, Z², and Z³ are each a radical independently selected from the group consisting of —H, —F, —Cl, —Br, —OH, —NH$_2$, and —(C(Z¹)(Z²)(Z³)), with a proviso that, if any one of Z¹, Z², or Z³ is —OH or —NH$_2$, then each of the remaining Z¹, Z², and Z³ is independently selected from the group consisting of —H and —(C(Z¹)(Z²)(Z³));
- R³ either forms said second fused ring structure with R² or is a radical selected from the group consisting of —H and a C1-C6 branched or straight chain alkyl represented by —(C(Z¹)(Z²)(Z³))$_n$, where $1 \leq n \leq 6$ and Z¹, Z², and Z³ are each a radical independently selected from the group consisting of —H, —F, —Cl, —Br, —OH, —NH$_2$, and —(C(Z¹)(Z²)(Z³)), with a proviso that, if any one of Z¹, Z², or Z³ is —OH or —NH$_2$, then each of the remaining Z¹, Z², and Z³ is independently selected from the group consisting of —H and —(C(Z¹)(Z²)(Z³);
- said first or second fused ring structure is either an aromatic or heteroaromatic 5- or 6-membered fused ring with or without C1-C6 branched or straight chain alkyl substituents, or a salt thereof.

3. A compound of formula I according to claim 1 represented by the following structure:

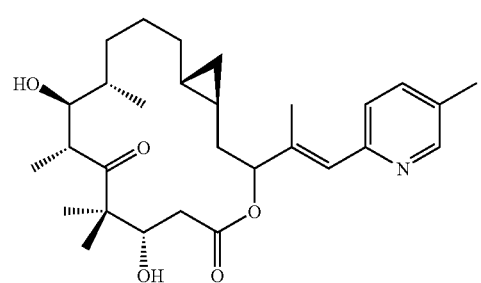

4. A compound of formula I-S according to claim 2 represented by the following structure:

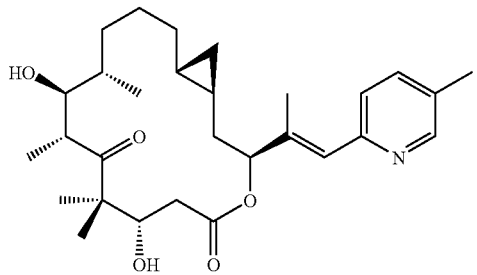

5. A compound of formula I according to claim 1 represented by the following structure:

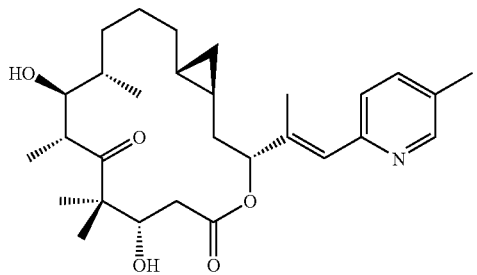

6. A compound of formula II (II)

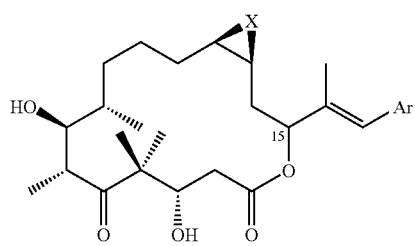

wherein
X is a diradical selected from the group consisting of —C(Y¹)(Y²)—, and —C(Y¹)(Y²)—C(Y¹)(Y²)—,
Y¹ and Y² are each radicals independently selected from the group consisting of —H, —F, —Cl and —Br; and
Ar is a radical represented by the following structure:

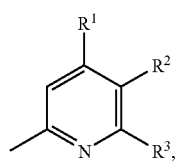

wherein
R¹ either forms a first fused ring structure with R² or is a radical selected from H and a C1-C6 branched or straight chain alkyl represented by —(C(Z¹)(Z²)(Z³))$_n$, where 1≦n≦6 and Z¹, Z², and Z³ are each a radical independently selected from the group consisting of —H, —F, —Cl, —Br, —OH, —NH₂, and —(C(Z¹)(Z²)(Z³)), with a proviso that, if any one of Z¹, Z², or Z³ is —OH or —NH₂, then each of the remaining Z¹, Z², and Z³ is independently selected from the group consisting of —H and —(C(Z¹)(Z²)(Z³));

R² either forms the first fused ring structure with R¹or forms a second fused ring structure with R³ or is a radical selected from the group consisting of —H and a C1-C6 branched or straight chain alkyl represented by —(C(Z¹)(Z²)(Z³))$_n$, where 1≦n≦6 and Z¹, Z², and Z³ are each a radical independently selected from the group consisting of —H, —F, —Cl, —Br, —OH, —NH₂, and —(C(Z¹)(Z²)(Z³)), with a proviso that, if any one of Z¹, Z², or Z³ is —OH or —NH₂, then each of the remaining Z¹, Z², and Z³ is independently selected from the group consisting of —H and —(C(Z¹)(Z²)(Z³));

R³ either forms said second fused ring structure with R² or is a radical selected from the group consisting of —H and a C1-C6 branched or straight chain alkyl represented by —(C(Z¹)(Z²)(Z³))$_n$, where 1≦n≦6 and Z¹, Z², and Z³ are each a radical independently selected from the group consisting of —H, —F, —Cl, —Br, —OH, —NH₂, and —(C(Z¹(Z²)(Z³)), with a proviso that, if any one of Z¹, Z², or Z³ is —OH or —NH₂, then each of the remaining Z¹, Z², and Z³ is independently selected from the group consisting of —H and —(C(Z¹)(Z²)(Z³));

said first or second fused ring structure is either an aromatic or heteroaromatic 5- or 6-membered fused ring with or without C1-C6 branched or straight chain alkyl substituents and the stereogenic center in 15-position can have R or S configuration, or a salt thereof.

7. A compound of formula II according to claim 6 wherein the stereogenic center in 15-position has S configuration, thus representing a compound of formula II-S, (II-S)

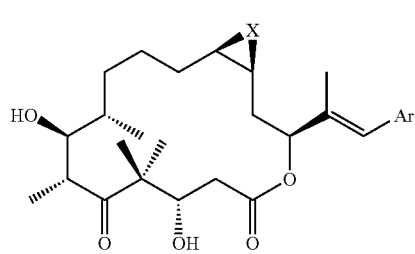

wherein
X is a diradical selected from the group consisting of —C(Y¹)(Y²)—, and —C(Y¹)(Y²)—C(Y¹)(Y²)—,
Y¹ and Y² are each radicals independently selected from the group consisting of —H, —F, —Cl and —Br; and
Ar is a radical represented by the following structure:

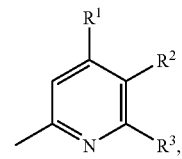

wherein:
R¹ either forms a first fused ring structure with R² or is a radical selected from —H and a C1-C6 branched or straight chain alkyl represented by —(C(Z$^1$)(Z$^2$)(Z$^3$))$_n$, where 1≦n≦6 and Z$^1$, Z$^2$, and Z$^3$ are each a radical independently selected from the group consisting of —H, —F, —Cl, —Br, —OH, —NH$_2$, and —(C(Z$^1$)(Z$^2$)(Z$^3$)), with a proviso that, if any one of Z$^1$, Z$^2$, or Z$^3$ is —OH or —NH$_2$, then each of the remaining Z$^1$, Z$^2$, and Z$^3$ is independently selected from the group consisting of —H and —(C(Z$^1$)(Z$^2$)(Z$^3$));

R$^2$ either forms the first fused ring structure with R1 or forms a second fused ring structure with R$^3$ or is a radical selected from the group consisting of —H and a C1-C6 branched or straight chain alkyl represented by —(C(Z$^1$)(Z$^2$)(Z$^3$))$_n$, where 1≦n≦6 and Z$^1$, Z$^2$, and Z$^3$ are each a radical independently selected from the group consisting of —H, —F, —Cl, —Br, —OH, —NH$_2$, and —(C(Z$^1$)(Z$^2$)(Z$^3$)), with a proviso that, if any one of Z$^1$, Z$^2$, or Z$^3$ is —OH or —NH$_2$, then each of the remaining Z$^1$, Z$^2$, and Z$^3$ is independently selected from the group consisting of —H and —(C(Z$^1$)(Z$^2$)(Z$^3$));

R$^3$ either forms said second fused ring structure with R$^2$ or is a radical selected from the group consisting of —H and a C1-C6 branched or straight chain alkyl represented by —(C(Z$^1$)(Z$^2$)(Z$^3$))$_n$, where 1≦n≦6 and Z$^1$, Z$^2$, and Z$^3$ are each a radical independently selected from the group consisting of —H, —F, —Cl, —Br, —OH, —NH$_2$, and —(C(Z$^1$)(Z$^2$)(Z$^3$)), with a proviso that, if any one of Z$^1$, Z$^2$, or Z$^3$ is —OH or —NH$_2$, then each of the remaining Z$^1$, Z$^2$, and Z$^3$ is independently selected from the group consisting of —H and —(C(Z$^1$)(Z$^2$)(Z$^3$));

said first or second fused ring structure is either an aromatic or heteroaromatic 5- or 6-membered fused ring with or without C1-C6 branched or straight chain alkyl substituents, or a salt thereof.

8. A compound of formula II according to claim 6 represented by the following structure:

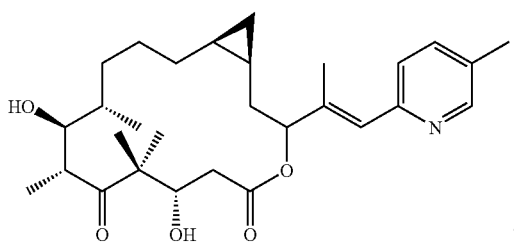

9. A compound of formula II-S according to claim 7 represented by the following structure:

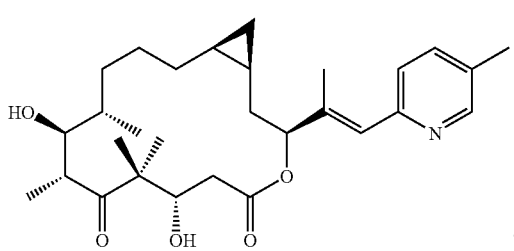

10. A compound of formula II according to claim 6 represented by the following structure:

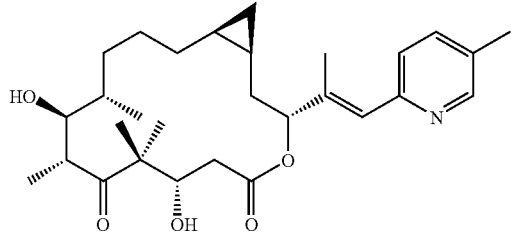

11. A compound of formula III

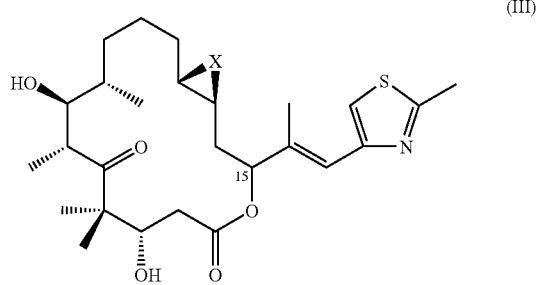

(III)

wherein

X is a diradical selected from the group consisting of —C(Y$^1$)(Y$^2$)—, and —C(Y$^1$)(Y$^2$)—C(Y$^1$)(Y$^2$)—, and Y$^1$ and Y$^2$ are each radicals independently selected from the group consisting of —H, —F, —Cl and —Br and the stereogenic center in 15-position can have R or S configuration, or a salt thereof.

12. A compound of formula III according to claim 11 wherein the stereogenic center in 15-position has S configuration, thus representing a compound of formula III-S

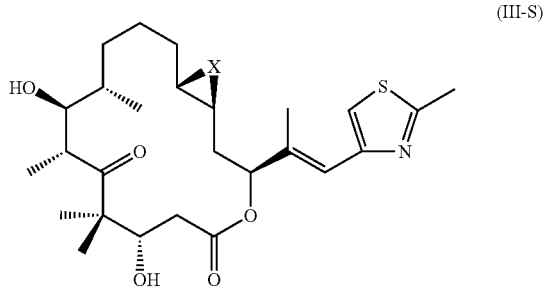

(III-S)

wherein

X is a diradical selected from the group consisting of —C(Y$^1$)(Y$^2$)—, and —C(Y$^1$)(Y$^2$)—C(Y$^1$)(Y$^2$)—, and Y$^1$ and Y$^2$ are each radicals independently selected from the group consisting of —H, —F, —Cl and —Br.

13. A compound of formula III-S according to claim 12 represented by the following structure:

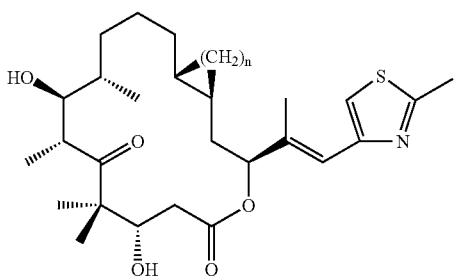

wherein n is either 1 or 2.

14. A compound of formula IV

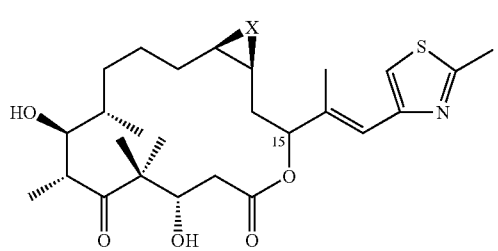

wherein
- X is a diradical selected from the group consisting of —C(Y¹)(Y²)—, and —C(Y¹)(Y²)—C(Y¹)(Y²)—, and
- Y¹ and Y² are each radicals independently selected from the group consisting of —H, —F, —Cl and —Br and
- the stereogenic center in 15-position can have R or S configuration,
- or a salt thereof.

15. A compound of formula IV according to claim 14 wherein the stereogenic center in 15-position has S configuration, thus representing a compound of formula IV-S,

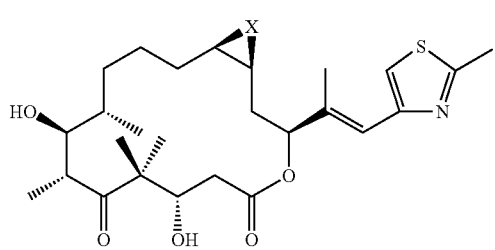

wherein
- X is a diradical selected from the group consisting of —C(Y¹)(Y²)—, and —C(Y¹)(Y²)—C(Y¹)(Y²)—, and
- Y¹ and Y² are each radicals independently selected from the group consisting of —H, —F, —Cl and —Br.

16. A compound of formula IV according to claim 14 represented by the following structure:

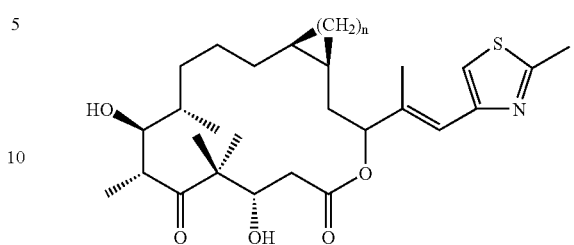

wherein n is either 1 or 2.

17. A compound of formula IV-S according to claim 15 represented by the following structure:

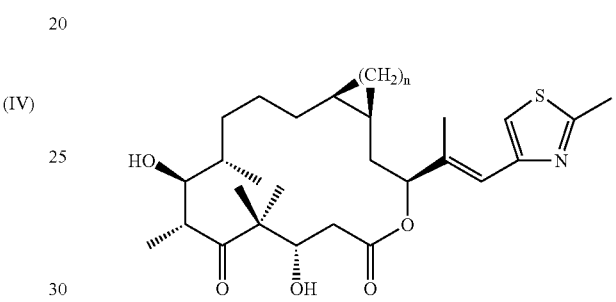

wherein n is either 1 or 2.

18. A compound of formula IV according to claim 14 represented by the following structure:

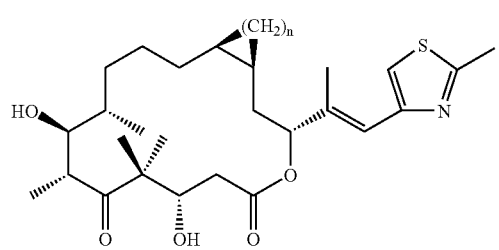

wherein n is either 1 or 2.

19. A process for killing a cancer cell comprising the step of contacting the cancer cell with a solution containing a cytotoxic concentration of any compound described by any one of claims 1 to 18.

20. A method for the treatment of a neoplastic disease, which comprises administering a compound of formula I, I-S, II, II-S, III, III-S, IV or IV-S according to any one of claims 1 to 18, or a pharmaceutically acceptable salt or a solvate or a hydrate of such a compound, in a quantity effective against said disease, to a warm-blooded animal requiring such treatment.

21. A pharmaceutical preparation, comprising a compound of formula I, I-S, II, II-S, III, III-S, IV or IV-S according to any one of claims 1 to 18, or a pharmaceutically acceptable salt or a solvate or a hydrate of such a compound, and at least one pharmaceutically acceptable carrier.

22. A process for the preparation of a compound of formula I,

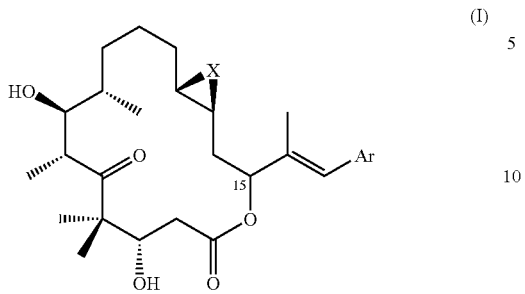

(I)

wherein
X is a diradical selected from the group consisting of —O—, —C(Y$^1$)(Y$^2$)—, and —C(Y$^1$)(Y$^2$)—C(Y$^1$)(Y$^2$)—,
Y$^1$ and Y$^2$ are each radicals independently selected from the group consisting of —H, —F, —Cl and —Br; and
Ar is a radical represented by the following structure:

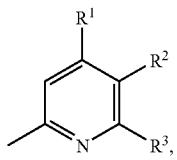

wherein
R$^1$ either forms a first fused ring structure with R$^2$ or is a radical selected from —H and a C1-C6 branched or straight chain alkyl represented by —(C(Z$^1$)(Z$^2$)(Z$^3$))$_n$, where $1 \leq n \leq 6$ and Z$^1$, Z$^2$, and Z$^3$ are each a radical independently selected from the group consisting of —H, —F, —Cl, —Br, —OH, —NH$_2$, and —(C(Z$^1$)(Z$^2$)(Z$^3$)), with a proviso that, if any one of Z$^1$, Z$^2$, or Z$^3$ is —OH or —NH$_2$, then each of the remaining Z$^1$, Z$^2$, and Z$^3$ is independently selected from the group consisting of —H and —(C(Z$^1$)(Z$^2$)(Z$^3$));
R$^2$ either forms the first fused ring structure with R$^1$ or forms a second fused ring structure with R$^3$ or is a radical selected from the group consisting of —H and a C1-C6 branched or straight chain alkyl represented by —(C(Z$^1$)(Z$^2$)(Z$^3$))$_n$, where $1 \leq n \leq 6$ and Z$^1$, Z$^2$, and Z$^3$ are each a radical independently selected from the group consisting of —H, —F, —Cl, —Br, —OH, —NH$_2$, and —(C(Z$^1$)(Z$^2$)(Z$^3$)), with a proviso that, if any one of Z$^1$, Z$^2$, or Z$^3$ is —OH or —NH$_2$, consisting of —H and —(C(Z$^1$)(Z$^2$)(Z$^3$));
R$^3$ either forms said second fused ring structure with R$^2$ or is a radical selected from the group consisting of —H and a C1-C6 branched or straight chain alkyl represented by —(C(Z$^1$)(Z$^2$)(Z$^3$))$_n$, where $1 \leq n \leq 6$ and Z$^1$, Z$^2$, and Z$^3$ are each a radical independently selected from the group consisting of —H, —F, —Cl, —Br, —OH, —NH$_2$, and —(C(Z$^1$)(Z$^2$)(Z$^3$)), with a proviso that, if any one of Z$^1$, Z$^2$, or Z$^3$ is —OH or —NH$_2$, then each of the remaining Z$^1$, Z$^2$, Z$^3$ and is independently selected from the group consisting of —H and —(C(Z$^1$)(Z$^2$)(Z$^3$));
said first or second fused ring structure is either an aromatic or heteroaromatic 5- or 6-membered fused ring with or without C1-C6 branched or straight chain alkyl substituents; and
the stereogenic center in 15-position can have R or S configuration, wherein a compound of the formula V

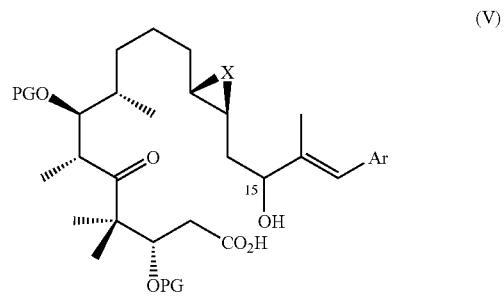

(V)

wherein X and Ar have the meaning as defined above for a compound of formula I and PG is a protecting group for a hydroxy function,
in a first step is condensed by a esterification reaction, optionally in the presence of a catalyst,
and in a second step the protecting group is detached thus furnishing a lactone of formula I.

23. A process for the preparation of a compound of formula III,

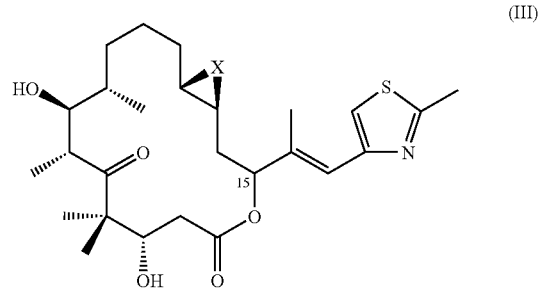

(III)

wherein
X is a diradical selected from the group consisting of —C(Y$^1$)(Y$^2$)—, and —C(Y$^1$)(Y$^2$)—C(Y$^1$)(Y$^2$)—, and
Y$^1$ and Y$^2$ are each radicals independently selected from the group consisting of —H, —F, —Cl and —Br and
the stereogenic center in 15-position can have R or S configuration,
wherein a compound of the formula VI

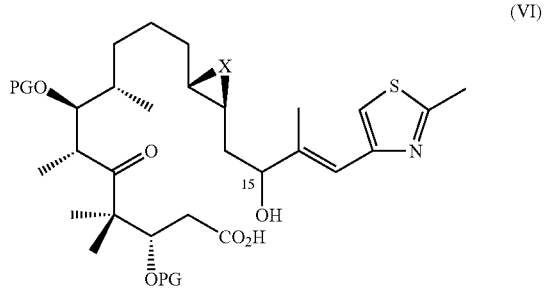

(VI)

wherein X has the meaning as defined above for a compound of formula III and PG is a protecting group for a hydroxy function,
in a first step is condensed by a esterification reaction, optionally in the presence of a catalyst,
and in a second step the protecting group is detached thus furnishing a lactone of formula III.

* * * * *